United States Patent
Zucherman et al.

(10) Patent No.: US 8,147,548 B2
(45) Date of Patent: Apr. 3, 2012

(54) INTERSPINOUS PROCESS IMPLANT HAVING A THREAD-SHAPED WING AND METHOD OF IMPLANTATION

(75) Inventors: James F. Zucherman, San Francisco, CA (US); Ken Y. Hsu, San Francisco, CA (US); Charles J. Winslow, Walnut Creek, CA (US); John J. Flynn, West Milford, NJ (US); Steve Mitchell, Pleasant Hill, CA (US); Scott A. Yerby, Montara, CA (US); John A. Markwart, Castro Valley, CA (US)

(73) Assignee: Kyphon Sarl, Neuchatel (CH)

( * ) Notice: Subject to any disclaimer, the term of this patent is extended or adjusted under 35 U.S.C. 154(b) by 1336 days.

(21) Appl. No.: 11/378,892

(22) Filed: Mar. 17, 2006

(65) Prior Publication Data
US 2006/0265066 A1 Nov. 23, 2006

Related U.S. Application Data

(60) Provisional application No. 60/663,922, filed on Mar. 21, 2005.

(51) Int. Cl.
*A61B 17/70* (2006.01)
*A61F 2/44* (2006.01)
(52) U.S. Cl. ............... 623/17.11; 606/248; 606/249
(58) Field of Classification Search ............ 606/60, 606/246–279; 623/17.11–17.16; 411/16, 411/24–25, 32, 340
See application file for complete search history.

(56) References Cited

U.S. PATENT DOCUMENTS

| | | | |
|---|---|---|---|
| 624,969 | A | 5/1899 | Peterson |
| 1,153,797 | A | 9/1915 | Kegreisz |
| 1,516,347 | A | 11/1924 | Pataky |
| 1,870,942 | A | 8/1932 | Beatty |
| 2,077,804 | A | 4/1937 | Morrison |
| 2,299,308 | A | 10/1942 | Creighton |
| 2,485,531 | A | 10/1949 | Dzus et al. |
| 2,607,370 | A | 8/1952 | Anderson |
| 2,677,369 | A | 5/1954 | Knowles |
| 2,685,877 | A | 8/1954 | Dobelle |
| 3,065,659 | A | 11/1962 | Eriksson et al. |

(Continued)

FOREIGN PATENT DOCUMENTS

DE 2821678 A1 11/1979

(Continued)

OTHER PUBLICATIONS

Benzel et al., "Posterior Cervical Interspinous Compression Wiring and Fusion for Mid to Low Cervical Spinal Injuries," J. Neurosurg., Jun. 1989, pp. 893-899, vol. 70.

(Continued)

*Primary Examiner* — Thomas C. Barrett
*Assistant Examiner* — Matthew Lawson

(57) ABSTRACT

Systems and method in accordance with an embodiment of the present invention can includes an implant comprising a spacer and a frame having a central body and a helical shaped wing extending from the central body. The frame can be positioned near about adjacent spinous processes, and can be rotated and urged so that the adjacent spinous processes pass within a groove of the wing, thereby allowing the wing to be arranged on an opposite side of the adjacent spinous processes. The spacer can then be arranged over the frame so that the spacer contacts and distracts the spinous processes, thereby limiting relative movement of the adjacent spinous processes during extension.

11 Claims, 22 Drawing Sheets

U.S. PATENT DOCUMENTS

| | | |
|---|---|---|
| 3,108,595 A | 10/1963 | Overment |
| 3,397,699 A | 8/1968 | Kohl |
| 3,426,364 A | 2/1969 | Lumb |
| 3,648,691 A | 3/1972 | Lumb et al. |
| 3,779,239 A | 12/1973 | Fischer et al. |
| 4,011,602 A | 3/1977 | Rybicki et al. |
| 4,237,875 A | 12/1980 | Termanini |
| 4,257,409 A | 3/1981 | Bacal et al. |
| 4,274,324 A | 6/1981 | Giannuzzi |
| 4,289,123 A | 9/1981 | Dunn |
| 4,327,736 A | 5/1982 | Inoue |
| 4,401,112 A | 8/1983 | Rezaian |
| 4,499,636 A | 2/1985 | Tanaka |
| 4,519,100 A | 5/1985 | Wills et al. |
| 4,553,273 A | 11/1985 | Wu |
| 4,554,914 A | 11/1985 | Kapp et al. |
| 4,573,454 A | 3/1986 | Hoffman |
| 4,592,341 A | 6/1986 | Omagari et al. |
| 4,599,086 A | 7/1986 | Doty |
| 4,604,995 A | 8/1986 | Stephens et al. |
| 4,611,582 A | 9/1986 | Duff |
| 4,632,101 A | 12/1986 | Freedland |
| 4,636,217 A | 1/1987 | Ogilvie et al. |
| 4,646,998 A | 3/1987 | Pate |
| 4,657,550 A | 4/1987 | Daher |
| 4,662,808 A | 5/1987 | Camilleri |
| 4,686,970 A | 8/1987 | Dove et al. |
| 4,704,057 A | 11/1987 | McSherry |
| 4,721,103 A | 1/1988 | Freedland |
| 4,759,670 A | 7/1988 | Linder et al. |
| 4,759,769 A | 7/1988 | Hedman et al. |
| 4,787,378 A | 11/1988 | Sodhi |
| 4,822,226 A | 4/1989 | Kennedy |
| 4,827,918 A | 5/1989 | Olerud |
| 4,834,600 A | 5/1989 | Lemke |
| 4,863,476 A | 9/1989 | Shepperd |
| 4,886,405 A * | 12/1989 | Blomberg ..................... 411/16 |
| 4,892,545 A | 1/1990 | Day et al. |
| 4,913,144 A | 4/1990 | Del Medico |
| 4,931,055 A | 6/1990 | Bumpus et al. |
| 4,932,975 A | 6/1990 | Main et al. |
| 4,969,887 A | 11/1990 | Sodhi |
| 5,000,166 A | 3/1991 | Karpf |
| 5,011,484 A | 4/1991 | Breard |
| 5,047,055 A | 9/1991 | Bao et al. |
| 5,059,193 A | 10/1991 | Kuslich |
| 5,092,866 A | 3/1992 | Breard et al. |
| 5,098,433 A | 3/1992 | Freedland |
| 5,171,278 A | 12/1992 | Pisharodi |
| 5,201,734 A | 4/1993 | Cozad et al. |
| 5,267,999 A | 12/1993 | Olerud |
| 5,290,312 A | 3/1994 | Kojimoto et al. |
| 5,306,275 A | 4/1994 | Bryan |
| 5,306,310 A | 4/1994 | Siebels |
| 5,312,405 A | 5/1994 | Korotko et al. |
| 5,316,422 A * | 5/1994 | Coffman ..................... 411/107 |
| 5,356,423 A | 10/1994 | Tihon et al. |
| 5,360,430 A | 11/1994 | Lin |
| 5,366,455 A | 11/1994 | Dove |
| 5,370,697 A | 12/1994 | Baumgartner |
| 5,390,683 A | 2/1995 | Pisharodi |
| 5,395,370 A | 3/1995 | Muller et al. |
| 5,401,269 A | 3/1995 | Buttner-Janz et al. |
| 5,403,316 A | 4/1995 | Ashman |
| 5,415,661 A | 5/1995 | Holmes |
| 5,437,672 A | 8/1995 | Alleyne |
| 5,437,674 A | 8/1995 | Worcel et al. |
| 5,439,463 A | 8/1995 | Lin |
| 5,454,812 A | 10/1995 | Lin |
| 5,456,689 A | 10/1995 | Kresch et al. |
| 5,458,638 A | 10/1995 | Kuslich et al. |
| 5,458,641 A | 10/1995 | Ramirez Jimenez |
| 5,480,442 A | 1/1996 | Bertagnoli |
| 5,496,318 A | 3/1996 | Howland et al. |
| 5,518,498 A | 5/1996 | Lindenberg et al. |
| 5,554,191 A | 9/1996 | Lahille et al. |
| 5,562,662 A | 10/1996 | Brumfield et al. |
| 5,562,735 A | 10/1996 | Margulies |
| 5,571,192 A | 11/1996 | Schonhoffer |
| 5,609,634 A | 3/1997 | Voydeville |
| 5,609,635 A | 3/1997 | Michelson |
| 5,628,756 A | 5/1997 | Barker, Jr. et al. |
| 5,630,816 A | 5/1997 | Kambin |
| 5,645,599 A | 7/1997 | Samani |
| 5,653,762 A | 8/1997 | Pisharodi |
| 5,653,763 A | 8/1997 | Errico et al. |
| 5,658,335 A | 8/1997 | Allen |
| 5,665,122 A | 9/1997 | Kambin |
| 5,674,295 A | 10/1997 | Ray et al. |
| 5,676,702 A | 10/1997 | Ratron |
| 5,683,463 A | 11/1997 | Godefroy et al. |
| 5,685,826 A | 11/1997 | Bonutti |
| 5,690,649 A | 11/1997 | Li |
| 5,693,100 A | 12/1997 | Pisharodi |
| 5,702,395 A | 12/1997 | Hopf |
| 5,702,452 A | 12/1997 | Argenson et al. |
| 5,702,455 A | 12/1997 | Saggar |
| 5,707,390 A | 1/1998 | Bonutti |
| 5,716,416 A | 2/1998 | Lin |
| 5,723,013 A | 3/1998 | Jeanson et al. |
| 5,725,341 A | 3/1998 | Hofmeister |
| 5,743,914 A | 4/1998 | Skiba |
| 5,746,762 A | 5/1998 | Bass |
| 5,755,797 A | 5/1998 | Baumgartner |
| 5,800,547 A | 9/1998 | Schafer et al. |
| 5,810,815 A | 9/1998 | Morales |
| 5,827,285 A | 10/1998 | Bramlet |
| 5,836,948 A | 11/1998 | Zucherman et al. |
| 5,849,004 A | 12/1998 | Bramlet |
| 5,860,977 A | 1/1999 | Zucherman et al. |
| 5,888,196 A | 3/1999 | Bonutti |
| 5,941,881 A | 8/1999 | Barnes |
| 5,976,186 A | 11/1999 | Bao et al. |
| 5,980,523 A | 11/1999 | Jackson |
| 6,022,376 A | 2/2000 | Assell et al. |
| 6,048,342 A | 4/2000 | Zucherman et al. |
| 6,068,630 A | 5/2000 | Zucherman et al. |
| 6,074,390 A | 6/2000 | Zucherman et al. |
| 6,093,207 A | 7/2000 | Pisharodi |
| 6,102,922 A | 8/2000 | Jakobsson et al. |
| 6,126,689 A | 10/2000 | Brett |
| 6,126,691 A | 10/2000 | Kasra et al. |
| 6,127,597 A | 10/2000 | Beyar et al. |
| 6,132,464 A | 10/2000 | Martin |
| 6,190,413 B1 | 2/2001 | Sutcliffe |
| 6,190,414 B1 | 2/2001 | Young |
| 6,214,037 B1 | 4/2001 | Mitchell et al. |
| 6,214,050 B1 | 4/2001 | Huene |
| 6,245,107 B1 | 6/2001 | Ferree |
| 6,293,949 B1 | 9/2001 | Justis et al. |
| 6,336,930 B1 | 1/2002 | Stalcup et al. |
| 6,348,053 B1 | 2/2002 | Cachia |
| 6,352,537 B1 | 3/2002 | Strnad |
| 6,364,883 B1 | 4/2002 | Santilli |
| 6,371,987 B1 | 4/2002 | Weiland et al. |
| 6,375,682 B1 | 4/2002 | Fleischmann et al. |
| 6,402,750 B1 | 6/2002 | Atkinson et al. |
| 6,402,751 B1 | 6/2002 | Hoeck et al. |
| 6,419,703 B1 | 7/2002 | Fallin et al. |
| 6,419,704 B1 | 7/2002 | Ferree |
| 6,432,130 B1 | 8/2002 | Hanson |
| 6,440,169 B1 | 8/2002 | Elberg et al. |
| 6,447,513 B1 | 9/2002 | Griggs |
| 6,451,019 B1 | 9/2002 | Zucherman et al. |
| 6,500,178 B2 | 12/2002 | Zucherman et al. |
| 6,511,508 B1 | 1/2003 | Shahinpoor et al. |
| 6,514,256 B2 | 2/2003 | Zucherman et al. |
| 6,520,991 B2 | 2/2003 | Huene |
| 6,554,833 B2 | 4/2003 | Levy |
| 6,582,433 B2 | 6/2003 | Yun |
| 6,582,467 B1 | 6/2003 | Teitelbaum et al. |
| 6,592,585 B2 | 7/2003 | Lee et al. |
| 6,626,944 B1 | 9/2003 | Taylor |
| 6,645,207 B2 | 11/2003 | Dixon et al. |
| 6,669,729 B2 | 12/2003 | Chin |
| 6,685,742 B1 | 2/2004 | Jackson |
| 6,695,842 B2 | 2/2004 | Zucherman et al. |

| Patent/Pub No. | Date | Name |
|---|---|---|
| 6,699,246 B2 | 3/2004 | Zucherman et al. |
| 6,709,435 B2 | 3/2004 | Lin |
| 6,723,126 B1 | 4/2004 | Berry |
| 6,730,126 B2 | 5/2004 | Boehm, Jr. et al. |
| 6,733,531 B1 | 5/2004 | Trieu |
| 6,733,534 B2 | 5/2004 | Sherman |
| 6,736,818 B2 | 5/2004 | Perren et al. |
| 6,743,257 B2 | 6/2004 | Castro |
| 6,758,863 B2 | 7/2004 | Estes et al. |
| 6,761,720 B1 | 7/2004 | Senegas |
| 6,770,096 B2 | 8/2004 | Bolger et al. |
| 6,783,530 B1 | 8/2004 | Levy |
| 6,835,205 B2 | 12/2004 | Atkinson et al. |
| 6,902,580 B2 | 6/2005 | Fallin et al. |
| 6,905,512 B2 | 6/2005 | Paes et al. |
| 6,946,000 B2 | 9/2005 | Senegas et al. |
| 6,981,975 B2 | 1/2006 | Michelson |
| 7,011,685 B2 | 3/2006 | Arnin et al. |
| 7,041,136 B2 | 5/2006 | Goble et al. |
| 7,048,736 B2 | 5/2006 | Robinson et al. |
| 7,070,598 B2 | 7/2006 | Lim et al. |
| 7,081,120 B2 | 7/2006 | Li et al. |
| 7,087,055 B2 | 8/2006 | Lim et al. |
| 7,087,083 B2 | 8/2006 | Pasquet et al. |
| 7,097,648 B1 | 8/2006 | Globerman et al. |
| 7,097,654 B1 | 8/2006 | Freedland |
| 7,101,375 B2 | 9/2006 | Zucherman et al. |
| 7,163,558 B2 | 1/2007 | Senegas et al. |
| 7,201,751 B2 | 4/2007 | Zucherman et al. |
| 7,217,293 B2 | 5/2007 | Branch, Jr. |
| 7,238,204 B2 | 7/2007 | Le Couedic et al. |
| 7,306,628 B2 | 12/2007 | Zucherman et al. |
| 7,335,203 B2 | 2/2008 | Winslow et al. |
| 7,377,942 B2 | 5/2008 | Berry |
| 7,431,735 B2 | 10/2008 | Liu et al. |
| 7,442,208 B2 | 10/2008 | Mathieu et al. |
| 7,445,637 B2 | 11/2008 | Taylor |
| 7,458,981 B2 | 12/2008 | Fielding et al. |
| 7,582,106 B2 | 9/2009 | Teitelbaum et al. |
| 7,604,652 B2 | 10/2009 | Arnin et al. |
| 7,611,316 B2 | 11/2009 | Panasik et al. |
| 7,621,950 B1 | 11/2009 | Globerman et al. |
| 7,658,752 B2 | 2/2010 | Labrom et al. |
| 7,749,252 B2 | 7/2010 | Zucherman et al. |
| 7,771,456 B2 | 8/2010 | Hartmann et al. |
| 7,862,615 B2 | 1/2011 | Carli et al. |
| 7,901,430 B2 | 3/2011 | Matsuura et al. |
| 2001/0016743 A1 | 8/2001 | Zucherman et al. |
| 2002/0143331 A1 | 10/2002 | Zucherman et al. |
| 2003/0040746 A1 | 2/2003 | Mitchell et al. |
| 2003/0045940 A1 | 3/2003 | Eberlein et al. |
| 2003/0065330 A1 | 4/2003 | Zucherman et al. |
| 2003/0153915 A1 | 8/2003 | Nekozuka et al. |
| 2004/0010312 A1 | 1/2004 | Enayati |
| 2004/0010316 A1 | 1/2004 | William et al. |
| 2004/0087947 A1 | 5/2004 | Lim et al. |
| 2004/0097931 A1 | 5/2004 | Mitchell |
| 2004/0106995 A1 | 6/2004 | LeCouedic et al. |
| 2004/0117017 A1 | 6/2004 | Pasquet et al. |
| 2004/0133204 A1 | 7/2004 | Davies |
| 2004/0133280 A1 | 7/2004 | Trieu |
| 2004/0158248 A1 | 8/2004 | Ginn |
| 2004/0167625 A1 | 8/2004 | Beyar et al. |
| 2004/0199255 A1 | 10/2004 | Mathieu et al. |
| 2004/0260397 A1 | 12/2004 | Lambrecht et al. |
| 2005/0010293 A1 | 1/2005 | Zucherman et al. |
| 2005/0033434 A1 | 2/2005 | Berry |
| 2005/0049708 A1 | 3/2005 | Atkinson et al. |
| 2005/0085814 A1 | 4/2005 | Sherman et al. |
| 2005/0143827 A1 | 6/2005 | Globerman et al. |
| 2005/0165398 A1 | 7/2005 | Reiley |
| 2005/0203512 A1 | 9/2005 | Hawkins et al. |
| 2005/0203519 A1 | 9/2005 | Harms et al. |
| 2005/0203624 A1 | 9/2005 | Serhan et al. |
| 2005/0228391 A1 | 10/2005 | Levy et al. |
| 2005/0245937 A1 | 11/2005 | Winslow |
| 2005/0261768 A1 | 11/2005 | Trieu |
| 2005/0267579 A1 | 12/2005 | Reiley et al. |
| 2005/0273166 A1 | 12/2005 | Sweeney |
| 2005/0288672 A1 | 12/2005 | Ferree |
| 2006/0004447 A1 | 1/2006 | Mastrorio et al. |
| 2006/0004455 A1 | 1/2006 | Leonard et al. |
| 2006/0015181 A1 | 1/2006 | Elberg |
| 2006/0064165 A1 | 3/2006 | Zucherman et al. |
| 2006/0084983 A1 | 4/2006 | Kim |
| 2006/0084985 A1 | 4/2006 | Kim |
| 2006/0084987 A1 | 4/2006 | Kim |
| 2006/0084988 A1 | 4/2006 | Kim |
| 2006/0085069 A1 | 4/2006 | Kim |
| 2006/0085070 A1 | 4/2006 | Kim |
| 2006/0085074 A1 | 4/2006 | Raiszadeh |
| 2006/0089654 A1 | 4/2006 | Lins et al. |
| 2006/0089719 A1 | 4/2006 | Trieu |
| 2006/0095136 A1 | 5/2006 | McLuen |
| 2006/0106381 A1 | 5/2006 | Ferree et al. |
| 2006/0106397 A1 | 5/2006 | Lins |
| 2006/0111728 A1 | 5/2006 | Abdou |
| 2006/0116690 A1 | 6/2006 | Pagano |
| 2006/0122620 A1 | 6/2006 | Kim |
| 2006/0129239 A1 | 6/2006 | Kwak |
| 2006/0136060 A1 | 6/2006 | Taylor |
| 2006/0142858 A1 | 6/2006 | Colleran et al. |
| 2006/0149242 A1 | 7/2006 | Kraus et al. |
| 2006/0182515 A1 | 8/2006 | Panasik et al. |
| 2006/0184247 A1 | 8/2006 | Edidin et al. |
| 2006/0184248 A1 | 8/2006 | Edidin et al. |
| 2006/0195102 A1 | 8/2006 | Malandain |
| 2006/0217726 A1 | 9/2006 | Maxy et al. |
| 2006/0224159 A1 | 10/2006 | Anderson |
| 2006/0224241 A1 | 10/2006 | Butler et al. |
| 2006/0235387 A1 | 10/2006 | Peterman |
| 2006/0235532 A1 | 10/2006 | Meunier et al. |
| 2006/0241601 A1 | 10/2006 | Trautwein et al. |
| 2006/0241613 A1 | 10/2006 | Bruneau et al. |
| 2006/0241643 A1 | 10/2006 | Lim et al. |
| 2006/0241757 A1 | 10/2006 | Anderson |
| 2006/0247623 A1 | 11/2006 | Anderson et al. |
| 2006/0247640 A1 | 11/2006 | Blackwell et al. |
| 2006/0264938 A1 | 11/2006 | Zucherman et al. |
| 2006/0271044 A1 | 11/2006 | Petrini et al. |
| 2006/0271049 A1 | 11/2006 | Zucherman et al. |
| 2006/0271061 A1 | 11/2006 | Beyar et al. |
| 2006/0282075 A1 | 12/2006 | Labrom et al. |
| 2006/0282079 A1 | 12/2006 | Labrom et al. |
| 2006/0293662 A1 | 12/2006 | Boyer, II et al. |
| 2006/0293663 A1 | 12/2006 | Walkenhorst et al. |
| 2007/0005064 A1 | 1/2007 | Anderson et al. |
| 2007/0010813 A1 | 1/2007 | Zucherman et al. |
| 2007/0032790 A1 | 2/2007 | Aschmann et al. |
| 2007/0043362 A1 | 2/2007 | Malandain et al. |
| 2007/0043363 A1 | 2/2007 | Malandain et al. |
| 2007/0073289 A1 | 3/2007 | Kwak et al. |
| 2007/0100340 A1 | 5/2007 | Lange et al. |
| 2007/0123861 A1 | 5/2007 | Dewey et al. |
| 2007/0142915 A1 | 6/2007 | Altarac et al. |
| 2007/0151116 A1 | 7/2007 | Malandain |
| 2007/0162000 A1 | 7/2007 | Perkins |
| 2007/0167945 A1 | 7/2007 | Lange et al. |
| 2007/0173822 A1 | 7/2007 | Bruneau et al. |
| 2007/0173823 A1 | 7/2007 | Dewey et al. |
| 2007/0191833 A1 | 8/2007 | Bruneau et al. |
| 2007/0191834 A1 | 8/2007 | Bruneau et al. |
| 2007/0191837 A1 | 8/2007 | Trieu |
| 2007/0191838 A1 | 8/2007 | Bruneau et al. |
| 2007/0198091 A1 | 8/2007 | Boyer et al. |
| 2007/0225807 A1 | 9/2007 | Phan et al. |
| 2007/0233068 A1 | 10/2007 | Bruneau et al. |
| 2007/0233074 A1 | 10/2007 | Anderson et al. |
| 2007/0233076 A1 | 10/2007 | Trieu |
| 2007/0233081 A1 | 10/2007 | Pasquet et al. |
| 2007/0233089 A1 | 10/2007 | DiPoto et al. |
| 2007/0250060 A1 | 10/2007 | Anderson et al. |
| 2007/0270823 A1 | 11/2007 | Trieu et al. |
| 2007/0270824 A1 | 11/2007 | Lim et al. |
| 2007/0270825 A1 | 11/2007 | Carls et al. |
| 2007/0270826 A1 | 11/2007 | Trieu et al. |
| 2007/0270827 A1 | 11/2007 | Lim et al. |
| 2007/0270828 A1 | 11/2007 | Bruneau et al. |

| | | | |
|---|---|---|---|
| 2007/0270829 A1 | 11/2007 | Carls et al. |
| 2007/0270834 A1 | 11/2007 | Bruneau et al. |
| 2007/0270874 A1 | 11/2007 | Anderson |
| 2007/0272259 A1 | 11/2007 | Allard et al. |
| 2007/0276368 A1 | 11/2007 | Trieu et al. |
| 2007/0276369 A1 | 11/2007 | Allard et al. |
| 2007/0276493 A1 | 11/2007 | Malandain et al. |
| 2007/0276496 A1 | 11/2007 | Lange et al. |
| 2007/0276497 A1 | 11/2007 | Anderson |
| 2007/0282443 A1 | 12/2007 | Globerman et al. |
| 2008/0021457 A1 | 1/2008 | Anderson et al. |
| 2008/0021460 A1 | 1/2008 | Bruneau et al. |
| 2008/0058934 A1 | 3/2008 | Malandain et al. |
| 2008/0097446 A1 | 4/2008 | Reiley et al. |
| 2008/0114357 A1 | 5/2008 | Allard et al. |
| 2008/0114358 A1 | 5/2008 | Anderson et al. |
| 2008/0114456 A1 | 5/2008 | Dewey et al. |
| 2008/0147190 A1 | 6/2008 | Dewey et al. |
| 2008/0161818 A1 | 7/2008 | Kloss et al. |
| 2008/0167685 A1 | 7/2008 | Allard et al. |
| 2008/0183209 A1 | 7/2008 | Robinson et al. |
| 2008/0183211 A1 | 7/2008 | Lamborne et al. |
| 2008/0183218 A1 | 7/2008 | Mueller et al. |
| 2008/0195152 A1 | 8/2008 | Altarac et al. |
| 2008/0215094 A1 | 9/2008 | Taylor |
| 2008/0221685 A9 | 9/2008 | Altarac et al. |
| 2008/0234824 A1 | 9/2008 | Youssef et al. |
| 2008/0262617 A1 | 10/2008 | Froehlich et al. |
| 2008/0281360 A1 | 11/2008 | Vittur et al. |
| 2008/0281361 A1 | 11/2008 | Vittur et al. |
| 2009/0062915 A1 | 3/2009 | Kohm et al. |
| 2009/0105766 A1 | 4/2009 | Thompson et al. |
| 2009/0105773 A1 | 4/2009 | Lange et al. |
| 2009/0234389 A1 | 9/2009 | Chuang et al. |
| 2009/0240283 A1 | 9/2009 | Carls et al. |
| 2009/0270918 A1 | 10/2009 | Attia et al. |
| 2010/0121379 A1 | 5/2010 | Edmond |
| 2010/0204732 A1 | 8/2010 | Aschmann et al. |

FOREIGN PATENT DOCUMENTS

| | | |
|---|---|---|
| DE | 3922044 A1 | 2/1991 |
| DE | 4012622 C1 | 7/1991 |
| EP | 0322334 B1 | 2/1992 |
| EP | 0767636 B1 | 1/1999 |
| EP | 1004276 A1 | 5/2000 |
| EP | 1011464 B1 | 6/2000 |
| EP | 1138268 A1 | 10/2001 |
| EP | 1148850 B1 | 10/2001 |
| EP | 1148851 B1 | 10/2001 |
| EP | 11302169 A1 | 4/2003 |
| EP | 1330987 A1 | 7/2003 |
| EP | 1552797 A2 | 7/2005 |
| EP | 1854433 A1 | 11/2007 |
| EP | 1905392 A1 | 4/2008 |
| EP | 1982664 A1 | 10/2008 |
| FR | 2623085 A1 | 5/1989 |
| FR | 2625097 A1 | 6/1989 |
| FR | 2681525 A1 | 3/1993 |
| FR | 2700941 A1 | 8/1994 |
| FR | 2703239 A1 | 10/1994 |
| FR | 2707864 A1 | 1/1995 |
| FR | 2717675 A1 | 9/1995 |
| FR | 2722087 A1 | 1/1996 |
| FR | 2722088 A1 | 1/1996 |
| FR | 2724554 A1 | 3/1996 |
| FR | 2725892 A1 | 4/1996 |
| FR | 2730156 A1 | 8/1996 |
| FR | 2731643 A1 | 9/1996 |
| FR | 2775183 A1 | 8/1999 |
| FR | 2799948 A1 | 4/2001 |
| FR | 2816197 A1 | 5/2002 |
| JP | 02-224660 | 9/1990 |
| JP | 09-075381 | 3/1997 |
| JP | 2003079649 | 3/2003 |
| SU | 988281 | 1/1983 |
| SU | 1484348 A1 | 6/1989 |
| WO | WO 94/26192 | 11/1994 |
| WO | WO 94/26195 | 11/1994 |
| WO | WO 97/18769 | 5/1997 |
| WO | WO 98/20939 | 5/1998 |
| WO | WO 99/26562 | 6/1999 |
| WO | WO 00/44319 | 8/2000 |
| WO | WO 01/54598 A1 | 8/2001 |
| WO | WO 03/057055 A1 | 7/2003 |
| WO | WO 2004/047689 A1 | 6/2004 |
| WO | WO 2004/047691 A1 | 6/2004 |
| WO | WO 2004/084743 A1 | 10/2004 |
| WO | WO 2004/084768 A2 | 10/2004 |
| WO | WO 2004/110300 A2 | 12/2004 |
| WO | WO 2005/009300 A1 | 2/2005 |
| WO | WO 2005/011507 A1 | 2/2005 |
| WO | WO 2005/044118 A1 | 5/2005 |
| WO | WO 2005/048856 A1 | 6/2005 |
| WO | WO 2005/110258 A1 | 11/2005 |
| WO | WO 2006/064356 A1 | 6/2006 |
| WO | WO 2007/034516 A1 | 3/2007 |
| WO | WO 2007052975 A1 | 5/2007 |
| WO | WO 2009/083276 A1 | 7/2009 |
| WO | WO 2009/083583 A1 | 7/2009 |
| WO | WO 2009/098536 A1 | 8/2009 |

OTHER PUBLICATIONS

Caserta et al., "Elastic Stabilization Alone or Combined with Rigid Fusion in Spinal Surgery: a Biomechanical Study and Clinical Experience Based on 82 Cases," Eur. Spine J., Oct. 2002, pp. S192-S197, vol. 11, Suppl. 2.

Christie et al., "Dynamic Interspinous Process Technology," SPINE, 2005, pp. S73-S78, vol. 30, No. 16S.

Cousin Biotech, Dispositif Intervertébral Amortissant, Jun. 1998, pp. 1-4.

Cousin Biotech, Dispositif Intervertebral Amortissant, Jun. 1998, pp. 1-4.

Dubois et al., "Dynamic Neutralization: A New Concept for Restabilization of the Spine," Lumbar Segmental Insability, Szpalski et al., eds., 1999, pp. 233-240, Lippincott Williams & Wilkins, Philadelphia, Pennsylvania.

Ebara et al., "Inoperative Measurement of Lumbar Spinal Instability," SPINE, 1992, pp. S44-S50, vol. 17, No. 3S.

Fassio et al., "Treatment of Degenerative Lumbar Spinal Instability L4-L5 by Interspinous Ligamentoplasty," Rachis, Dec. 1991, pp. 465-474, vol. 3, No. 6.

Fassio, "Mise au Point Sur la Ligamentoplastie Inter-Epineuse Lombaire Dans les Instabilites," Maîtrise Orthopédique, Jul. 1993, pp. 18, No. 25.

Garner et al., "Development and Preclinical Testing of a New Tension-Band Device for the Spine: the Loop System," Eur. Spine J., Aug. 7, 2002, pp. S186-S191, vol. 11, Suppl. 2.

Guang et al., "Interspinous Process Segmental Instrumentation with Bone-Button-Wire for Correction of Scoliosis," Chinese Medical J., 1990, pp. 721-725, vol. 103.

Guizzardi et al., "The use of DIAM (Interspinous Stress-Breaker Device) in the Prevention of Chronic Low Back Pain in Young Patients Operated on for Large Dimension Lumbar Disc Herniation," 12th Eur. Congress of Neurosurgery (EANS), Sep. 7-12, 2003, pp. 835-839, Lisbon, Portugal.

Hambly et al., "Tension Band Wiring-Bone Grafting for Spondylolysis and Spondylolisthesis," SPINE, 1989, pp. 455-460, vol. 14, No. 4.

Kiwerski, "Rehabilitation of Patients with Thoracic Spine Injury Treated by Spring Alloplasty," Int. J. Rehab. Research, 1983, pp. 469-474, vol. 6, No. 4.

Laudet et al., "Comportement Bio-Mécanique D'Un Ressort Inter-Apophysaire Vertébral Postérieur Analyse Expérimentale Due Comportement Discal En Compression Et En Flexion/Extension," Rachis, 1993, vol. 5, No. 2.

Mah et al., "Threaded K-Wire Spinous Process Fixation of the Axis for Modified Gallie Fusion in Children and Adolescents," J. Pediatric Othopaedics, 1989, pp. 675-679, vol. 9.

Mariottini et al., "Preliminary Results of a Soft Novel Lumbar Intervertebral Prothesis (DIAM) in the Degenerative Spinal Pathology," Acta Neurochirurgia, Advanced Peripheral Nerve Surgery and Minimal Invasive Spinal Surgery, Alexandre et al., eds., 2005, pp. 129-131, vol. 92, Suppl.

McDonnell et al., "Posterior Atlantoaxial Fusion: Indications and Techniques," Techniques in Spinal Fusion and Stabilization, Hitchon et al., eds., 1995, pp. 92-106, Ch. 9, Thieme, New York.

Minns et al., "Preliminary Design and Experimental Studies of a Novel Soft Implant for Correcting Sagittal Plane Instability in the Lumbar Spine," SPINE, 1997, pp. 1819-1825, vol. 22, No. 16.

Müller, "Restauration Dynamique de la Stabilité Rachidienne," Tiré de la Sulzer Technical Review, Jan. 1999, Sulzer Management Ltd, Winterthur, Switzerland.

Pennal et al., "Stenosis of the Lumbar Spinal Canal," Clinical Neurosurgery: Proceedings of the Congress of Neurological Surgeons, St. Louis, Missouri, 1970, Tindall et al., eds., 1971, Ch. 6, pp. 86-105, vol. 18.

Petrini et al., "Analisi Di Un'Esperienza Clinica Con Un Impianto Posteriore Ammortizzante," S.O.T.I.M.I. Società di Ortopedia e Traumatologia dell'Italia Meridionale e Insulare 90° Congresso, Jun. 21-23, 2001, Paestum.

Petrini et al., "Stabilizzazione Elastica," Patologia Degenerativa del Rachide Lombare, Oct. 5-6, 2001, Rimini.

Porter, "Spinal Stenosis and Neurogenic Claudication," SPINE, Sep. 1, 1996, pp. 2046-2052, vol. 21, No. 17.

Pupin et al., "Clinical Experience with a Posterior Shock-Absorbing Implant in Lumbar Spine," World Spine 1: First Interdisciplinary World Congress on Spinal Surgery and Related Disciplines, Aug. 27-Sep. 1, 2000, Berlin, Germany.

Rengachary et al., "Cervical Spine Stabilization with Flexible, Multistrand Cable System," Techniques in Spinal Fusion and Stabilization, Hitchon et al., eds., 1995, pp. 79-81, Ch. 7, Thieme, New York.

Richards et al., "The Treatment Mechanism of an Interspinous Process Implant for Lumbar Neurogenic Intermittent Claudication," SPINE, 2005, pp. 744-749, vol. 30, No. 7.

Schiavone et al., "The use of Disc Assistance Prosthesis (DIAM) in Degenerative Lumbar Pathology: Indications, Technique, Results," Italian J. Spinal Disorders, 2003, pp. 213-220, vol. 3, No. 2.

Schlegel et al., "The Role of Distraction in Improving the Space Available in the Lumbar Stenotic Canal and Foramen," SPINE, 1994, pp. 2041-2047, vol. 19, No. 18.

Senegas et al., "Le Recalibrage du Canal Lombaire, Alternative à la Laminectomie dans le Traitement des Sténoses du Canal Lombaire," Revue de Chirurgie Orthopédique, 1988, pp. 15-22.

Senegas et al., "Stabilisation Lombaire Souple," Instabilité Vertébrales Lombaires, Gastambide, ed., 1995, pp. 122-132, Expansion Scientifique Française, Paris, France.

Senegas, "La Ligamentoplastie Inter Vertébrale Lombaire, Alternative a L'Arthrodèse," La Revue de Medécine Orthopédique, Jun. 1990, pp. 33-35, No. 20.

Senegas, "La Ligamentoplastie Intervertébrale, Alternative àL'arthrodèse dans le Traitement des Instabilités Dégénératives," Acta Othopaedica Belgica, 1991, pp. 221-226, vol. 57, Suppl. I.

Senegas, "Mechanical Supplementation by Non-Rigid Fixation in Degenerative Intervertebral Lumbar Segments: the Wallis System," Eur. Spine J., 2002, p. S164-S169, vol. 11, Suppl. 2.

Senegas, "Rencontre," Maîtrise Orthopédique, May 1995, pp. 1-3, No. 44.

Serhan, "Spinal Implants: Past, Present, and Future," 19th International IEEE/EMBS Conference, Oct. 30-Nov. 2, 1997, pp. 2636-2639, Chicago, Illinois.

Spadea et al., "Interspinous Fusion for the Treatment of Herniated Intervertebral Discs: Utilizing a Lumbar Spinous Process as a Bone Graft," Annals of Surgery, 1952, pp. 982-986, vol. 136, No. 6.

Taylor et al., "Analyse d'une expérience clinique d'un implant postérieur amortissant," Rachis Revue de Pathologie Vertébrale, Oct./Nov. 1999, vol. 11, No. 4-5, Gieda Inter Rachis.

Taylor et al., "Technical and Anatomical Considerations for the Placement of a Posterior Interspinous Stabilizer," 2004, pp. 1-10, Medtronic Sofamor Danek USA, Inc., Memphis, Tennessee.

Taylor, "Biomechanical Requirements for the Posterior Control of the Centers of Rotation," Swiss Spine Institute International Symposium: Progress in Spinal Fixation, Jun. 21-22, 2002, pp. 1-2, Swiss Spine Institute, Bern, Switzerland.

Taylor, "Non-Fusion Technologies of the Posterior Column: A New Posterior Shock Absorber," International Symposium on Intervertebral Disc Replacement and Non-Fusion-Technology, May 3-5, 2001, Spine Arthroplasty.

Taylor, "Présentation à un an d'un dispositif amortissant d'assistance discale," 5èmes journées Avances & Controverses en pathologie rachidienne, Oct. 1-2, 1998, Faculté Libre de Médecine de Lille.

Tsuji et al., "Ceramic Interspinous Block (CISB) Assisted Anterior Interbody Fusion," J. Spinal Disorders, 1990, pp. 77-86, vol. 3, No. 1.

Vangilder, "Interspinous, Laminar, and Facet Posterior Cervical Bone Fusions," Techniques in Spinal Fusion and Stabilization, Hitchon et al., eds., 1995, pp. 135-146, Ch. 13, Thieme, New York.

Voydeville et al., "Experimental Lumbar Instability and Artificial Ligament," Eur. J. Orthop. Surg. Traumatol., Jul. 15, 2000, pp. 167-176, vol. 10.

Voydeville et al., "Lumbar Instability Treated by Intervertebral Ligamentoplasty with Smooth Wedges," Orthopédie Traumatologie, 1992, pp. 259-264, vol. 2, No. 4.

Waldemar Link, "Spinal Surgery: Instrumentation and Implants for Spinal Surgery," 1981, Link America Inc., New Jersey.

Wiltse et al., "The Treatment of Spinal Stenosis," Clinical Orthopaedics and Related Research, Urist, ed., Mar.-Apr. 1976, pp. 83-91, No. 115.

Wisneski et al., "Decompressive Surgery for Lumbar Spinal Stenosis," Seminars in Spine Surgery, Wiesel, ed., Jun. 1994, pp. 116-123, vol. 6, No. 2.

Zucherman et al., "Clinical Efficacy of Spinal Instrumentation in Lumbar Degenerative Disc Disease," SPINE, Jul. 1992, pp. 834-837, vol. 17, No. 7.

Kramer et al., "Intervetertebral Disk Diseases: Causes, Diagnosis, Treatment and Prophylaxis," pp. 244-249, Medical, 1990.

Zdeblick et al., "Two-Point Fixation of the Lumbar Spine Differential Stability in Rotation," SPINE, 1991, pp. S298-S301, vol. 16, No. 6, Supplement.

Anasetti et al., "Spine Stability After Implantation of an Interspinous Device: An In Vitro and Finite Element Biomechanical Study," J. Neurosurg. Spine, Nov. 2010, vol. 13, pp. 568-575.

Bellini et al., "Biomechanics of the Lumbar Spine Afer Dynamic Stabilization," J. Spinal Discord Tech., 2006, vol. 00, No. 00, pp. 1-7.

Buric et al., "DIAM Device for Low Back Pain in Degenerative Disc Disease 24 Months Follow-up," Advances in Minimally Invasive Surgery and Therapy for Spine and Nerves, Alexandre et al., eds., 2011, pp. 177-182, Spinger-Verlat/Wien.

Phillips et al., "Biomechanics of Posterior Dynamic Stabiling Device (DIAM) After Facetectomy and Disectomy," The Spine Journal, 2006, vol. 6, pp. 714-722.

Taylor et al., "Device for Intervertebral Assisted Motion: Technique and Intel Results," 22 Neurosurg. Focus, Jan. 2007, vol. 22, No. 1, pp. 1-6.

Wilke et al., "Biomedical Effect of Different Lumbar Interspinous Implants on Flexibilty and Intradiscal Pressure," Eur Spine J., Vo. 17, published online Jun. 27, 2008, pp. 1049-1056.

Zhao et al., "Efficacy of the Dynamic Interspinous Assisted Motion System in Clinical Treatment of Degenerative Lumbar Disease," Chin. Med. J., 2010, vol. 123, No. 21, pp. 2974-2977.

* cited by examiner ns of human cervical spine*, Spine, vol. 17 at 1131 (Nov. 10, 1992). In contrast, neck flexion increases the foraminal area. Humpreys, S. C. et al., at 1105.

INTERSPINOUS PROCESS IMPLANT HAVING A THREAD-SHAPED WING AND METHOD OF IMPLANTATION

CLAIM TO PRIORITY

This application claims the benefit of U.S. Provisional Patent Application No. 60/663,922 entitled INTERSPINOUS PROCESS IMPLANT HAVING A THREAD-SHAPED WING AND METHOD OF IMPLANTATION, by Zucherman et al., filed Mar. 21, 2005.

CROSS-REFERENCE TO RELATED APPLICATIONS

This U.S. Patent Application incorporates by reference all of the following co-pending applications and issued patents:

U.S. patent application Ser. No. 10/850,267, entitled "Distractible Interspinous Process Implant and Method of Implantation," filed May 20, 2004;

U.S. Pat. No. 6,419,676, entitled "Spine Distraction Implant and Method," issued Jul. 16, 2002 to Zucherman, et al.;

U.S. Pat. No. 6,451,019, entitled "Supplemental Spine Fixation Device and Method," issued Sep. 17, 2002 to Zucherman, et al.;

U.S. Pat. No. 6,582,433, entitled "Spine Fixation Device and Method," issued Jun. 24, 2003 to Yun;

U.S. Pat. No. 6,652,527, entitled "Supplemental Spine Fixation Device and Method," issued Nov. 25, 2003 to Zucherman, et al;

U.S. Pat. No. 6,695,842, entitled "Interspinous Process Distraction System and Method with Positionable Wing and Method," issued Feb. 24, 2004 to Zucherman, et al;

U.S. Pat. No. 6,699,246, entitled "Spine Distraction Implant," issued Mar. 2, 2004 to Zucherman, et al; and U.S. Pat. No. 6,712,819, entitled "Mating Insertion Instruments for Spinal Implants and Methods of Use," issued Mar. 30, 2004 to Zucherman, et al.

TECHNICAL FIELD

This invention relates to interspinous process implants.

BACKGROUND OF THE INVENTION

The spinal column is a bio-mechanical structure composed primarily of ligaments, muscles, vertebrae and intervertebral disks. The bio-mechanical functions of the spine include: (1) support of the body, which involves the transfer of the weight and the bending movements of the head, trunk and arms to the pelvis and legs, (2) complex physiological motion between these parts, and (3) protection of the spinal cord and the nerve roots.

As the present society ages, it is anticipated that there will be an increase in adverse spinal conditions which are characteristic of older people. By way of example only, with aging comes an increase in spinal stenosis (including, but not limited to, central canal and lateral stenosis), and facet arthropathy. Spinal stenosis results in a reduction foraminal area (i.e., the available space for the passage of nerves and blood vessels) which compresses the cervical nerve roots and causes radicular pain. Humpreys, S. C. et al., *Flexion and traction effect on C5-C6 foraminal space*, Arch. Phys. Med. Rehabil., vol. 79 at 1105 (September 1998). Another symptom of spinal stenosis is myelopathy, which results in neck pain and muscle weakness. Id. Extension and ipsilateral rotation of the neck further reduces the foraminal area and contributes to pain, nerve root compression and neural injury. Id.; Yoo, J. U. et al., *Effect of cervical spine motion on the neuroforaminal dimensions of human cervical spine*, Spine, vol. 17 at 1131 (Nov. 10, 1992). In contrast, neck flexion increases the foraminal area. Humpreys, S. C. et al., at 1105.

Pain associated with stenosis can be relieved by medication and/or surgery. It is desirable to eliminate the need for major surgery for all individuals, and in particular, for the elderly.

Accordingly, a need exists to develop spine implants that alleviate pain caused by spinal stenosis and other such conditions caused by damage to, or degeneration of, the spine. Such implants would distract, or increase the space between, the vertebrae to increase the foraminal area and reduce pressure on the nerves and blood vessels of the spine.

A further need exists for development of a minimally invasive surgical implantation method for spine implants that preserves the physiology of the spine.

Further, a need exists for an implant that accommodates the distinct anatomical structures of the spine, minimizes further trauma to the spine, and obviates the need for invasive methods of surgical implantation. Additionally, a need exists to address adverse spinal conditions that are exacerbated by spinal extension and/or flexion.

DETAILED DESCRIPTION

Interspinous Implants

Figure 1A:
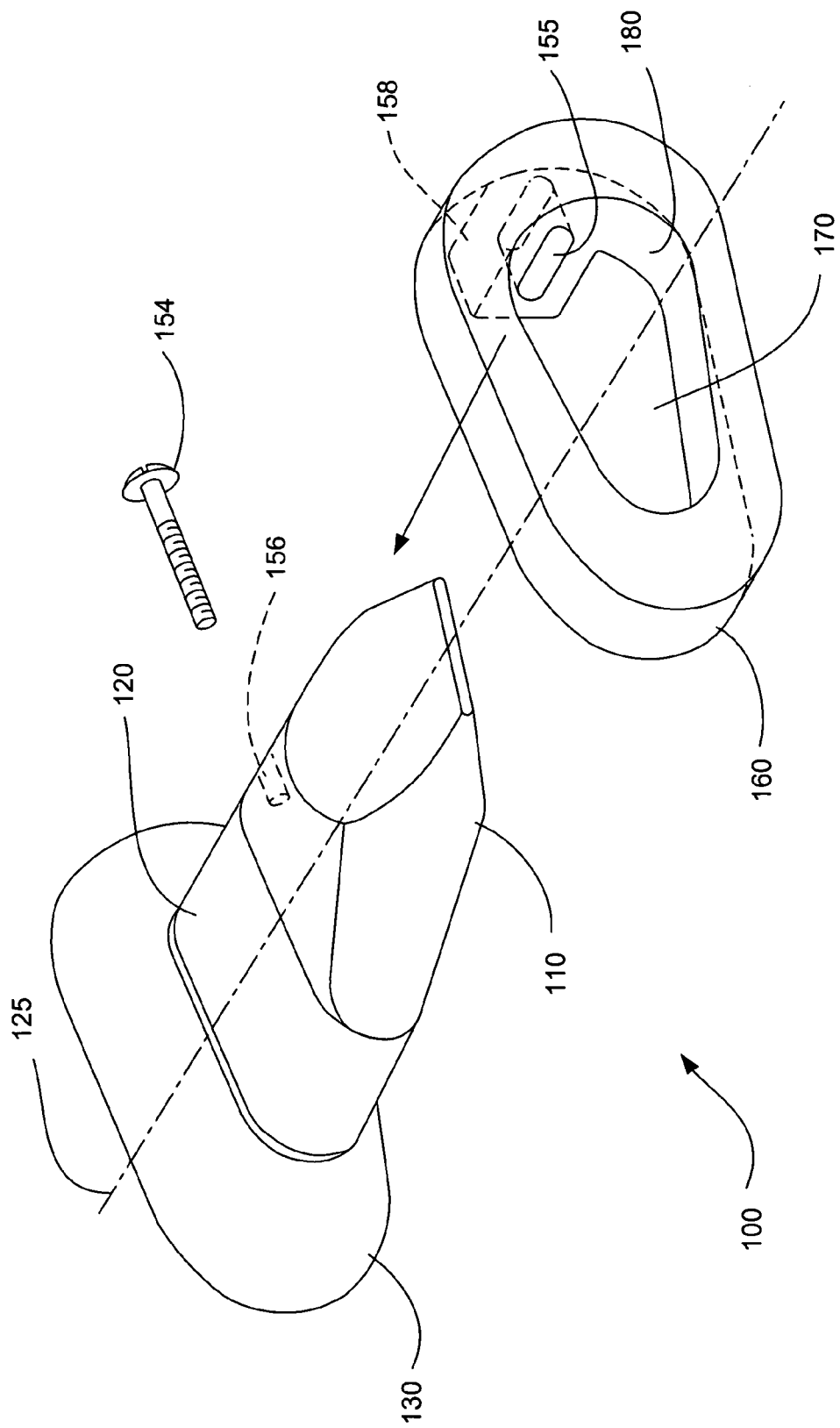
FIG. 1A is a perspective view of an implant including a spacer having a tear-drop shaped cross-section, a distraction guide, a first wing, and a second wing connectable with the distraction guide.

FIG. 1A is a perspective view of an implant as described in U.S. patent application Ser. No. 10/850,267, filed May 20, 2004, incorporated herein by reference. The implant 100 comprises a first wing 130, a spacer 120, and a lead-in tissue expander (also referred to herein as a distraction guide) 110. The distraction guide 110 in this particular embodiment is wedge-shaped, i.e., the implant has an expanding cross-section from a proximal end of the implant 100 to a region 150 where the guide 110 joins with the spacer 120 (referencing for the figures is based on the point of insertion of the implant between spinous processes). As such, the distraction guide 110 functions to initiate distraction of the soft tissue and the spinous processes when the implant 100 is surgically inserted between the spinous processes. It is to be understood that the distraction guide 110 can be pointed and the like, in order to facilitate insertion of the implant 100 between the spinous processes of adjacent cervical vertebrae. It is advantageous that the insertion technique disturb as little of the bone and surrounding tissue or ligaments as possible in order to reduce trauma to the site and promote early healing, and prevent destabilization of the normal anatomy. For embodiments such as those of FIGS. 1A and 1B, there is no requirement to remove any of the bone of the spinous processes and no requirement to sever, or remove from the body, ligaments and tissues immediately associated with the spinous processes. For example, it is unnecessary to sever the supraspinal ligament of the lower vertebrae or the ligamentum nuchae (which corresponds to the supraspinal ligament) which partially cushions the spinous processes of the upper cervical vertebrae.

As can be seen, the spacer 120 can be teardrop-shaped in cross-section perpendicular to a longitudinal axis 125 of the implant 100. In this way, the shape of the spacer 120 can roughly conform to a wedge-shaped space, or a portion of the space, between adjacent spinous processes within which the implant 100 is to be positioned. As shown in FIG. 1A, the spacer 120 (and the first wing 108) is shaped to accommodate the anatomical form or contour of spinous processes (and/or laminae) of the C6 and C7 vertebra for placement between such spinous processes (i.e., the C6-C7 motion segment). The same shape or variations of this shape can be used to accommodate other motion segments, for example in the thoracic or lumbar regions. In other embodiments the spacer 120 can have alternative shapes such as circular, wedge, oval, ovoid, football, and rectangular with rounded corners, and other shapes. The shape of the spacer 120 can be selected for a particular patient so that the physician can position the implant 100 as close as possible to the anterior portion of the surface of the spinous process. The shape selected for the spacer 120 can affect the contact surface area of the implant 100 and the spinous processes that are to be subject to distraction. Increasing the contact surface area between the implant 100 and the spinous processes can distribute a load force between the spinous frame and the implant 100.

The first wing 130 is likewise teardrop-shaped in cross-section perpendicular to a longitudinal axis 125 of the spacer 120 and distraction guide 110. The dimensions of the first wing 130 can be larger than that of the spacer 120, particularly along the axis of the spine, and can limit or block lateral displacement of the implant 100 in the direction of insertion along the longitudinal axis 125. As with the spacer 120, the first wing 130 can have other cross-sectional shapes, such as elliptical, wedge, circular, oval, ovoid, football, and rectangular with rounded corners and other shapes.

The implant 100 of FIG. 1A further includes an adjustable wing 160 (also referred to herein as a second wing) separate from the distraction guide 110, the spacer 120 and the first wing 130. The second wing 160 is connectable with the distraction guide 110 (and/or the spacer 120) once the implant 100 is positioned between adjacent spinous processes. The second wing 160, similar to the first wing 130, can limit or block lateral displacement of the implant 100, however displacement is limited or blocked in the direction opposite insertion. When both the first wing 130 and the second wing 160 are connected with the implant 100 and the implant 100 is positioned between adjacent spinous processes, a portion of the spinous processes can be sandwiched between the first wing 130 and the second wing 160, limiting displacement along the longitudinal axis 125. As can be seen, the second wing 160 can be teardrop-shaped in cross-section. A lip 180 defining a space 170 through the second wing 160 allows the second wing 160 to pass over the distraction guide 110 to meet and connect with the distraction guide 110 and/or the spacer 120. The second wing 160 is then secured to the distraction guide 110 and/or the spacer 120. The second wing 160, can be designed to be interference-fit onto the spacer 120 or a portion of the distraction guide 110 adjacent to the spacer 120. Where the second wing 160 is interference-fit, there is no additional attachment device to fasten the second wing 160 relative to the remainder of the implant 100.

Alternatively, various fasteners can be used to secure the second wing 160 relative to the remainder of the implant 100. For example, FIG. 1A illustrates an embodiment of an implant 100 including a teardrop-shaped second wing 160 having a tongue 158 at the posterior end of the second wing 160. A bore 155 is disposed through the tongue 158, and is aligned with a corresponding bore 156 on the spacer 120 when the second wing 160 is brought into position by surgical insertion relative to the rest of the implant 100. A threaded screw 154 can be inserted through the aligned bores 155,156 in a posterior-anterior direction to secure the second wing 160 to the spacer 120. The direction of insertion from a posterior to an anterior direction has the screw 154 engaging the bores 155,156 and the rest of the implant 100 along a direction that is generally perpendicular to the longitudinal axis 125. This orientation is most convenient when the physician is required to use a screw 154 to secure the second wing 160 to the rest of the implant 100. The second wing 160 can further be secured to the spacer 120 by some other mechanism, for example such as a flexible hinge (not shown) with a protrusion that engages an indentation of one of the distraction guide 110 and the spacer 120. Alternatively, the second wing 160 can be secured to one of the distraction guide 110 and the spacer 120 by still some other mechanism.

Figure 1B:
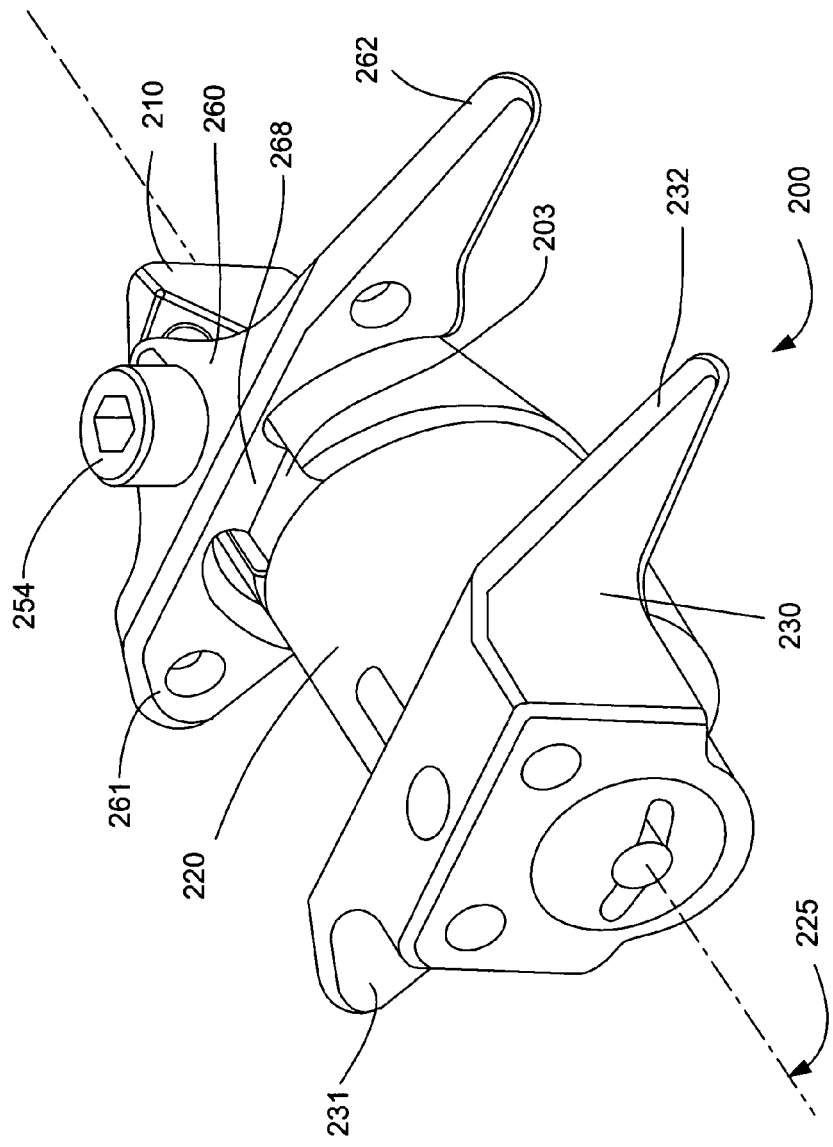
FIG. 1B is a perspective view of an implant including a rotatable spacer having an elliptical cross-section, a distraction guide, a first wing, and a second wing connectable with the distraction guide.

FIG. 1B is a perspective view of an implant as described in U.S. Pat. No. 6,695,842 to Zucherman, et al., incorporated herein by reference. The implant 200 has a main body that includes a spacer 220, a first wing 230, a lead-in tissue expander 210 (also referred to herein as a distraction guide) and an alignment track 203. The main body of the implant 200 is inserted between adjacent spinous processes and remains in place (where desired) without attachment to the bone or ligaments.

The distraction guide 210 includes a tip from which the distraction guide 210 expands, the tip having a diameter sufficiently small such that the tip can pierce an opening in an interspinous ligament and/or can be inserted into a small initial dilated opening. The diameter and/or cross-sectional area of the distraction guide 210 gradually increases until it is substantially similar to the diameter of the spacer 220. The tapered front end eases the ability of a physician to urge the implant 200 between adjacent spinous processes. When urging the main body of the implant 200 between adjacent spinous processes, the front end of the distraction guide 210 distracts the adjacent spinous processes and dilates the interspinous ligament so that a space between the adjacent spinous processes is approximately the diameter of the spacer 220.

As shown in FIG. 1B, the spacer 220 is elliptically shaped in cross-section, and can swivel so that the spacer 220 can self-align relative to the uneven surfaces of the spinous processes. Self-alignment can ensure that compressive loads are distributed across the surface of the bone. As contemplated in Zucherman '842, the spacer 220 can have, for example, a diameter of six millimeters, eight millimeters, ten millimeters, twelve millimeters and fourteen millimeters. These diameters refer to the height by which the spacer 220 distracts and maintains apart the spinous process. For an elliptically shaped spacer 220, the selected height (i.e., diameter) is the minor dimension measurement across the ellipse. The major dimension is transverse to the alignment of the spinous process, one above the other.

The first wing 230 has a lower portion 231 and an upper portion 232. The upper portion 232 is shaped to accommodate the anatomical form or contour of spinous processes (and/or laminae) of the L4 (for an L4-L5 placement) or L5 (for an L5-S1 placement) vertebra. The same shape or variations of this shape can be used to accommodate other motion segments, such as motion segments in the cervical and thoracic regions. The lower portion 231 can also be rounded to accommodate the spinous processes. The lower portion 231 and upper portion 232 of the first wing 230 act as a stop mechanism when the implant 200 is inserted between adjacent spinous processes. The implant 200 cannot be inserted beyond the surfaces of the first wing 230. Additionally, once the implant 200 is inserted, the first wing 230 can prevent some side-to-side, or posterior-to-anterior movement of the implant 200.

As with the implant 100 of FIG. 1A, the implant 200 of FIG. 1B further includes a second wing 260. Similar to the first wing 230, the second wing 260 includes a lower portion 261 and an upper portion 262 sized and/or shaped to accommodate the anatomical form or contour of the spinous processes and/or lamina. The second wing 260 can be secured to the main body of the implant 200 with a fastener 254. The second wing 260 also has an alignment tab 268. When the second wing 260 is initially placed on the main body of the implant 200, the alignment tab 268 engages the alignment track 203. The alignment tab 268 slides within the alignment track 203 and helps to maintain the adjustable wing 260 substantially parallel with the first wing 230. When the main body of the implant 200 is inserted into the patient and the second wing 260 has been attached, displacement along the longitudinal axis 225 in either the direction of insertion or the direction opposite insertion can be limited or blocked. Further, the second wing 260 also can prevent some side-to-side, or posterior-to-anterior movement.

For both the implant 100 of FIG. 1A and the implant 200 of FIG. 1B, where a second wing 160,260 is connected with the implant 100,200 after the implant 100,200 is positioned between the spinous processes, a procedure for positioning such an implant 100,200 and subsequently connecting the second wing 160,260 with the implant 100,200 can require a bilateral approach wherein a physician must access both sides of the interspinous ligament, a first side to pierce and/or distract the interspinous ligament and position the implant 100,200 so that the movement in the direction of insertion is satisfactorily limited by the first wing 130,230, and a second side to attach the second wing 160,260 such that movement in the direction opposite insertion is satisfactorily limited by the second wing 160,260.

Implants Having a Lead-In Screw

Referring to FIGS. 2A through 3C, implants 300 and methods for positioning such implants in accordance with the present invention can include, in an embodiment, a frame 302 having a central body 304 extending along a longitudinal axis 325 of the implant 300. The central body 304 can include a distraction guide 306 at a proximal end of the central body 304. The distraction guide 306 can have a tapered shape so that the distraction guide 306 can pierce and/or distract an interspinous ligament associated with the targeted motion segment. A first wing 330 extends from a distal end of the central body 304 and acts to limit or block movement of the implant 300 along the longitudinal axis 325 in the direction of insertion.

A substantially thread-shaped lead-in screw (also referred to herein as a second wing) 360 extends from the periphery of the central body 304 distally located relative to the distraction guide 306. For example, the second wing can be helical shaped, wherein a helical shape is generally a three-dimensional curve that lies on a cylinder or a cone, so that its angle to a plane perpendicular to the axis is constant. Helical shapes as described herein need not lie along a constant angle, but rather can lie along an angle that varies. A helical shape need only include a curve that has a gap 361 (also referred to herein as a groove) between overlapping surfaces such that structures related to the adjacent spinous processes and the spinous processes can pass within the groove 361. It is to be understood that a lead-in screw shape other than helical is within the spirit and scope of the invention. For example, a shape with a constant diameter thread, or with different or constant thread pitches can be used. Generally and preferably the second wing 360 can have an outer diameter that steadily increases from near the proximal end of the central body 304 distally toward the first wing 330. The second wing 360 terminates so that a spacer 320 (FIG. 2B) can be arranged between the second wing 360 and the first wing 330. The helical shape of the second wing 360 can facilitate implantation between adjacent spinous processes 2,4 (shown in FIGS. 3A-3E) from one or more incisions formed on one side of an interspinous ligament 6 extending between the adjacent spinous processes 2,4.

Implantation can be accomplished in such embodiments as described above by initially piercing or distracting the interspinous ligament 6 with the distraction guide 306, and subsequently rotating the central body 304. One or both of the interspinous ligament 6 and the adjacent spinous processes 2,4 slip within the groove 361 of the helically shaped second wing 360 as the central body 304 is rotated and the central body 304 is drawn or urged along the longitudinal axis 325 in the direction of insertion. The interspinous ligament 6 and/or associated spinous processes 2,4 travels along the groove 361 and therefore along the central body 304, causing the second wing 360 to be positioned, when the implant 300 is seated, at an opposite side of the interspinous ligament 6 from the first wing 330 such that the interspinous ligament 6 is disposed between the first wing 330 and the second wing 360 along the longitudinal axis 325. Arranging the interspinous ligament 6, and/or the associated spinous processes 2,4 between the first wing 330 and the second wing 360 limits or blocks movement along the longitudinal axis 325.

In some embodiments, the distraction guide 306 can have a generally conical shape, rather than a wedge-shape as described above in reference to FIGS. 1A and 1B. Where the distraction guide 306 includes a wedge-shape, rotation of the central body 304 can cause the distraction guide 306 to distract the adjacent spinous processes 2,4 and/or interspinous ligament 6 a distance according to the major dimension of the distraction guide 306.

Figure 2A:
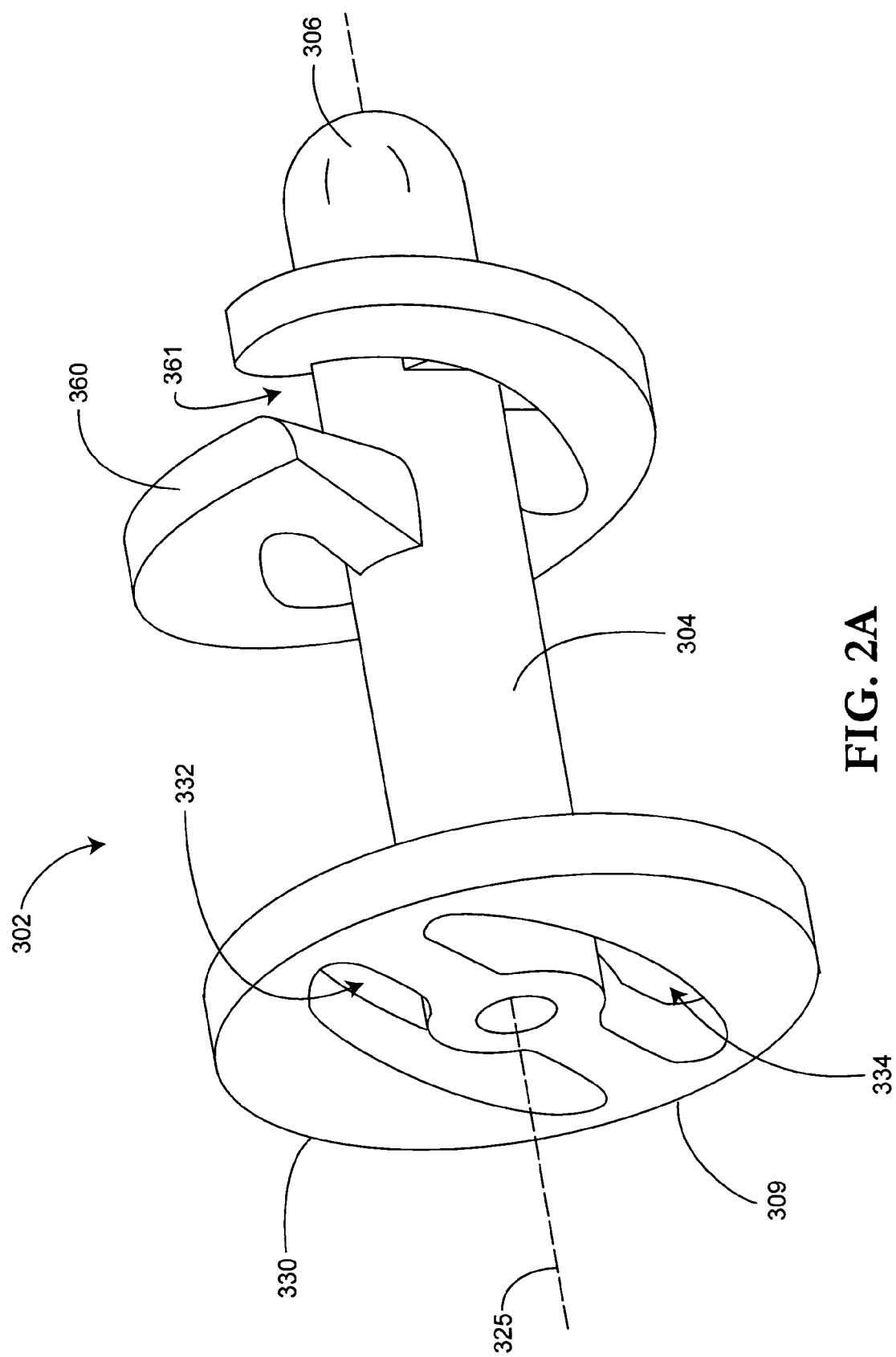
FIG. 2A is a perspective view of a frame of an implant in accordance with an embodiment of the present invention.

Referring to FIG. 2A, as with the distraction guide 306, the first wing 330 has a rounded shape, having substantially the same minor and major dimension. The first wing 330 is shaped so that the first wing 330 can rotate along with the central body 304 while minifying interference from surrounding structures. Further, the rounded shape of the first wing 330 can accommodate slots as described below, while providing a surface to contact the adjacent spinous processes 2,4 during implantation, thereby limiting movement along the longitudinal axis 325 in the direction of insertion. However, in other embodiments, the first wing 330 need not have a rounded shape.

The first wing 330 can include one or more slots to receive a spacer 320 so that the spacer 320 can be arranged over the central body 304 between the second wing 360 and the first wing 330. As shown, the first wing 330 includes two slots 332,334 having a substantially arced shape, and arranged in opposition to one another. The maximum distance between the peripheries of the slots 332,334 can substantially define a minor (or alternatively a major) dimension of the spacer 320. The slots 332,334 preferably have inner surfaces that transition to the outer surface of the central body 304, so that when a spacer 320 is urged through the slots 332,334, the spacer 320 abuts the central body 304, thereby allowing a portion of a load to be transferred to the central body 304. In other embodiments, one or more slots can be disposed through the first wing 330 and can be shaped as desired, such that the one or more slots having the same or different geometries.

Figure 2B:
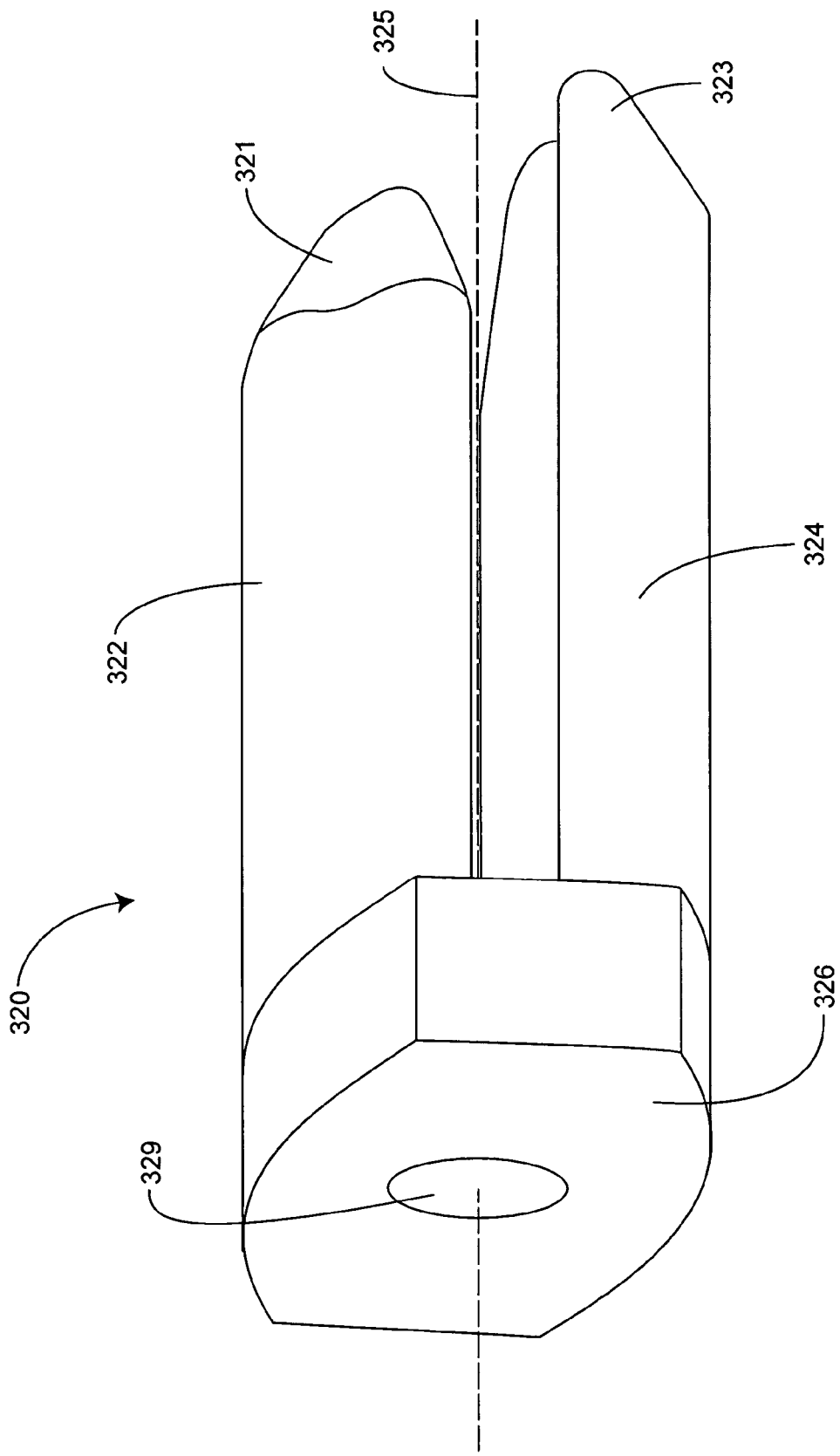
FIG. 2B is a perspective view of a spacer for use with the frame of FIG. 2A.

FIG. 2B is a perspective view of the spacer 320 having a geometry adapted to be received over the frame 302 described above. The spacer 320 includes a top portion 322 and a bottom portion 324. (It should be noted that some components of the implant are referred to herein as "top" and "bottom" components; however, positional modifiers are attached merely to distinguish between similar components and are not meant to limit use of the invention.) The top portion 322 and the bottom portion 324 have outer surfaces that support a respective adjacent spinous process 2,4 and inner surfaces that abut the central body 304. As shown, a portion of the inner surfaces of the top portion 322 and the bottom portion 324 are grooved so as to approximately conform with a shape of the central body 304, thereby spreading a load across the outer surface of the central body 304. The outer surfaces are arced, and generally shaped to resemble the outer periphery of the slots 332,334 of the first wing 330. In other embodiments, for example where the central body is trapezoidal, or otherwise shaped, the top portion 322, bottom portion 324, and corresponding slots 332,334 can be similarly shaped to accommodate the central body 304. Alternatively, the central body 304 can have an irregular or non-symmetrical shape to prevent incorrect mating of the spacer 320 with the frame 302. One of ordinary skill in the art will appreciate the myriad variations with which the structures can be shaped.

As can be seen, the top portion 322 and the bottom portion 324 include respective lead-in tissue expanders 321,323 (also referred to herein as a distraction guides). The distraction guide 321,323 for the top portion 322 and the bottom portion 324 can taper at the proximal end of the spacer 320, thereby allowing the distraction guide 306 to distract one or both of the adjacent spinous processes 2,4 and/or interspinous ligament 6.

As can be seen, the top portion 322 and the bottom portion 324, taken together in cross-section perpendicular to a longitudinal axis 325, can have a split teardrop shape, similar to a cross-section of the spacer 120 of FIG. 1A. In this way, the shape of the spacer 320 can roughly conform to a wedge-shaped space, or a portion of the space, between adjacent spinous processes within which the implant 300 is to be positioned. The same shape or variations of this shape can be used to accommodate different motion segments and/or different patients, as described above. In other embodiments the spacer 320 can have alternative shapes such as circular, elliptical, wedge, oval, ovoid, football, and rectangular with rounded corners, and other shapes. The shape of the spacer 320 can be selected for a particular patient so that the physician can position the implant 300 as close as possible to the anterior portion of the surface of the spinous process. The shape selected for the spacer 320 can affect the contact surface area of the implant 300 and the spinous processes that are to be subject to distraction. Increasing the contact surface area between the implant 300 and the spinous processes can distribute a load force between the spinous frame and the implant 300.

The top portion 322 and the bottom portion 324 extend from a base 326 and are fixed in relative position by the base 326. As can be seen, the bottom portion 324 extends farther than the top portion 322. As will be described in further detail below, the top portion 322 is truncated in length along the longitudinal axis 325 relative to the bottom portion 324 to avoid contacting the second wing 360 which in the embodiment shown in FIG. 2A spirals to a termination point at the upper surface of the central body 304. An additional advantage with the truncated top portion 322 is that the spinous processes are distracted more gradually, first with the bottom portion 324 and then with the top portion 322 as the spacer 320 is inserted into the frame 302. The base 326 can have a length along the longitudinal axis 325 as desired, and preferably having a length sufficient to support the top portion 322 and the bottom portion 324 in an at least semi-rigid position relative to one another. The base 326 can include a cavity 329 for receiving one or both of an insertion tool and a fastener (not shown). The cavity 329 can correspond to a threaded cavity 309 disposed in the central body 304 so that, for example, the frame 302 and the spacer 320 can be fixedly attached, with by way of example only a screw, once the spacer 320 is seated.

Figure 2C:
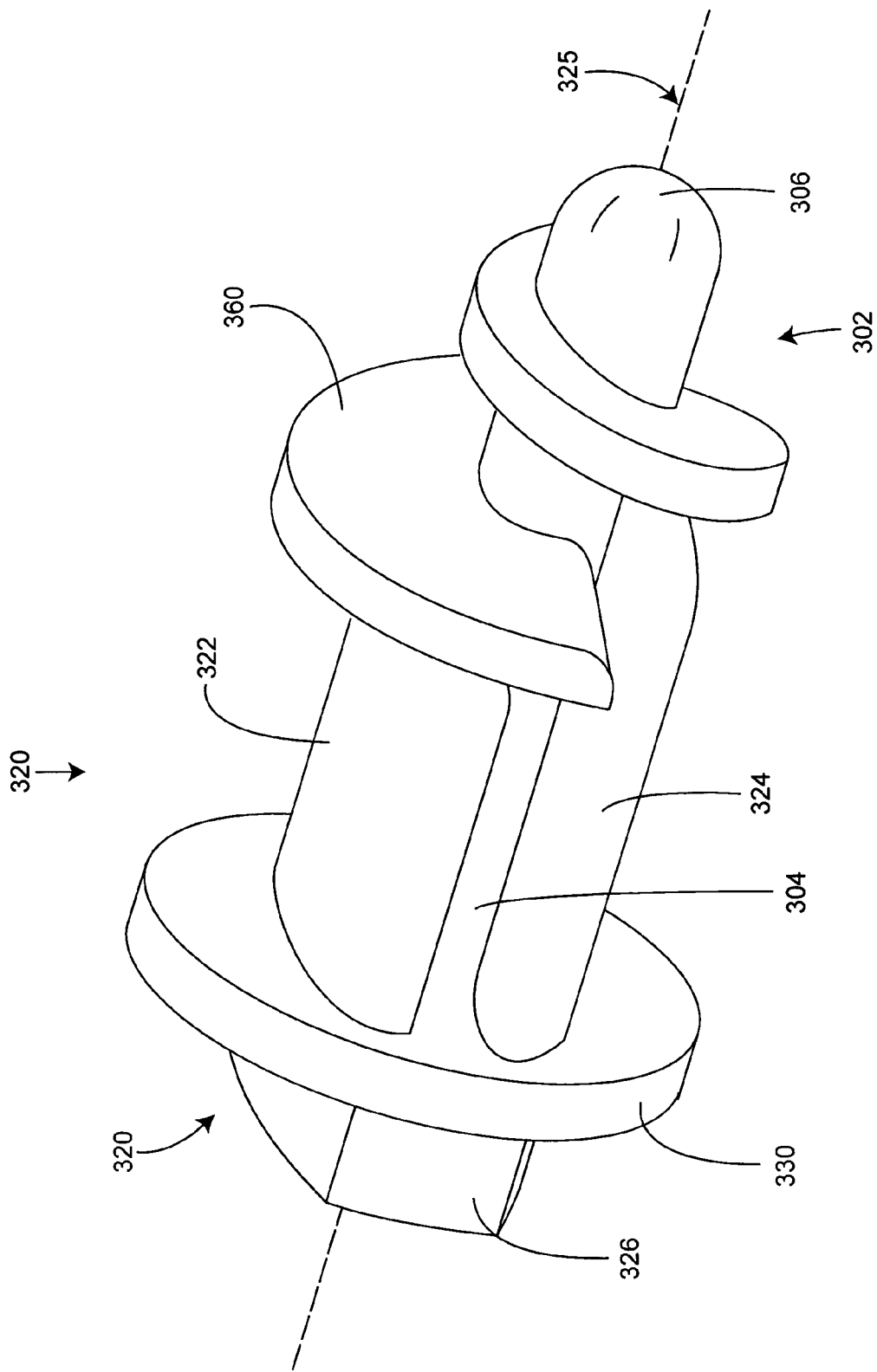
FIG. 2C is a perspective view of the spacer of FIG. 2B seated within the frame of FIG. 2A.

FIG. 2C is a perspective view of the implant 300 wherein the spacer 320 is seated within the frame 302 and arranged over the central body 304. As can be seen, the bottom portion 324 of the spacer 320 extends further than the top portion 322, and is unobstructed by the second wing 360, which spirals partially above the bottom portion 324. The first wing 330 and the second wing 360 have major dimensions approximately along the axis of the spine that are larger than the major dimension of the spacer 320, thereby blocking or limiting movement of the implant 300 along the longitudinal axis 325.

Figure 3A:
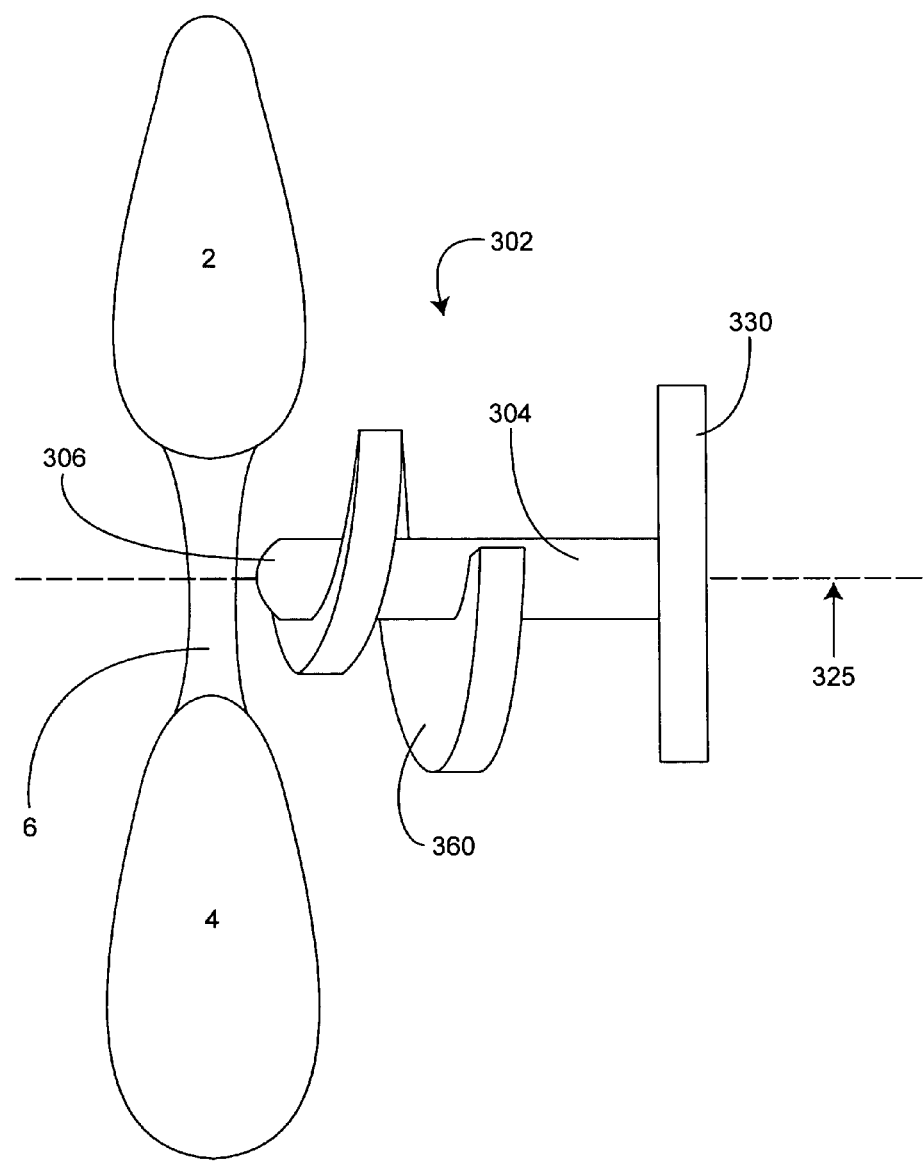
FIG. 3A is a partial cross-sectional posterior view of the frame of the implant of FIGS. 2A-2C positioned adjacent to an interspinous ligament disposed between adjacent spinous processes.
Figure 3B:
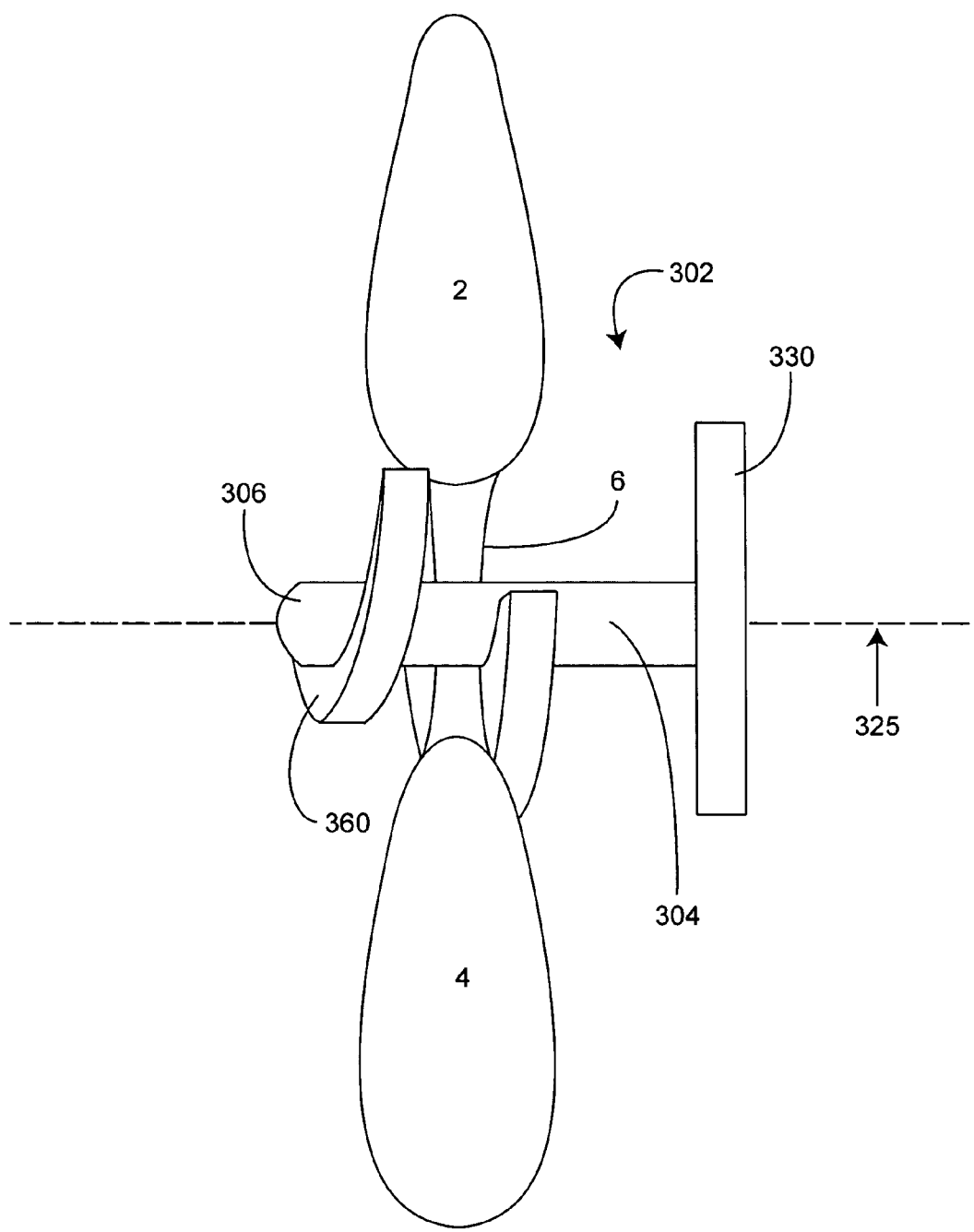
FIG. 3B partial cross-sectional posterior view of the frame of the implant of FIGS. 2A-2C rotated so that the interspinous ligament is disposed between a portion of the helical shaped second wing and the first wing along a longitudinal axis of the implant.
Figure 3C:
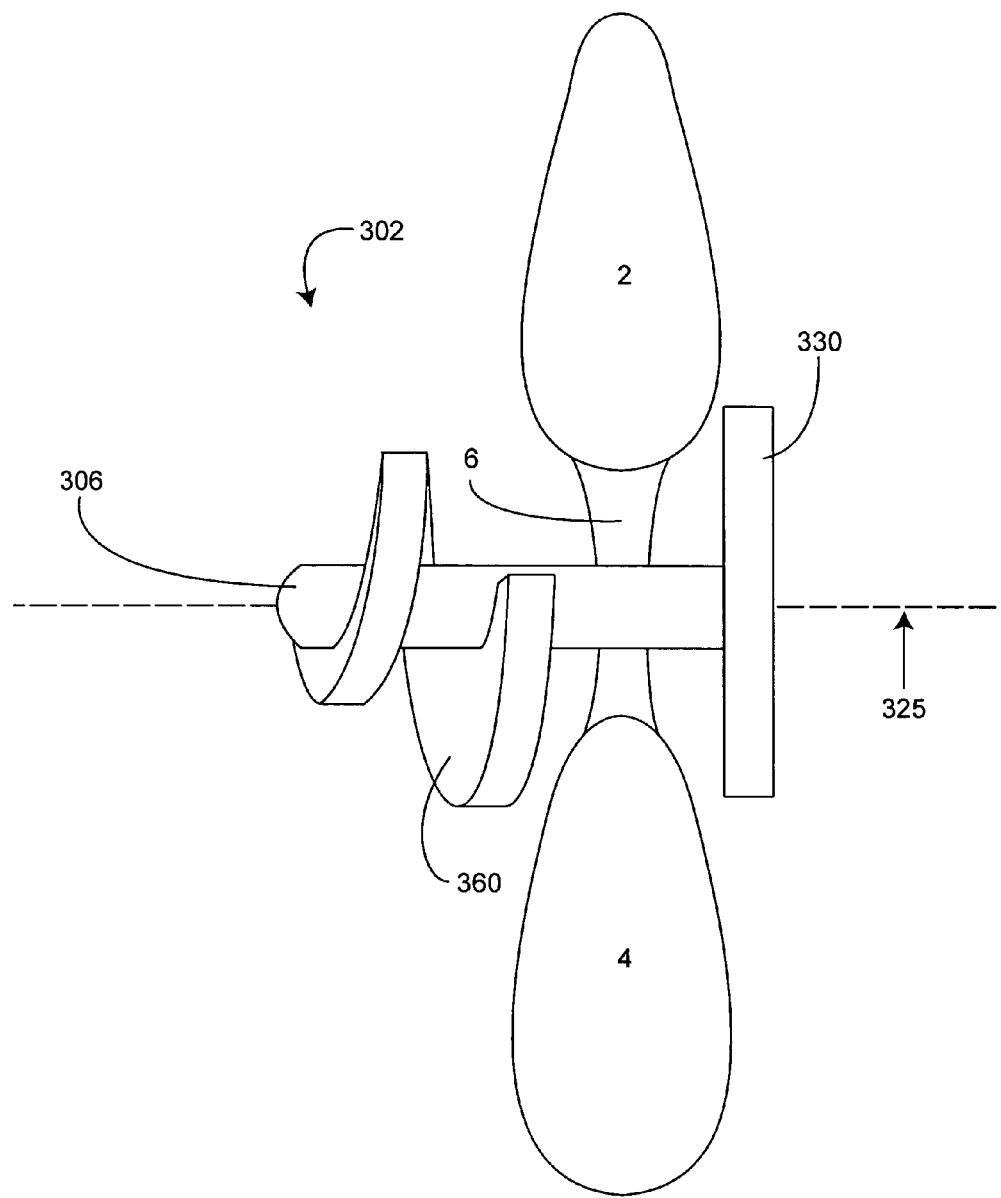
FIG. 3C partial cross-sectional posterior view of the frame of the implant of FIGS. 2A-2C rotated so that the interspinous ligament is disposed between the entire helical shaped second wing and the first wing along the longitudinal axis.

FIGS. 3A through 3E are partial cross-sectional posterior views illustrating the implant 300 being positioned between adjacent spinous processes. FIG. 3A illustrates the distraction guide of the frame 302 positioned adjacent to the interspinous ligament 6 of the targeted motion segment. The frame 302 can be urged against the interspinous ligament 6 to pierce and/or distract the interspinous ligament 6. The frame 302 can further be urged into the interspinous ligament 6 along the longitudinal axis 325 until the second wing 360 contacts the interspinous ligament 6. Referring to FIG. 3B, the frame 302 can then be rotated and urged toward the interspinous ligament 6 so that the second wing 360 passes through the interspinous ligament 6, which is thereby positioned between a portion of the second wing 360 and the first wing 330 along the longitudinal axis 325. The interspinous ligament 6 and the adjacent spinous processes 2,4 are substantially disposed within a groove 361 between the surfaces of the second wing 360 that overlap along the longitudinal axis 325. Referring to FIG. 3C, the frame 302 can be further rotated and urged into the interspinous ligament 6 until the entire second wing 360 is substantially arranged so that the interspinous ligament 6 is disposed between the first wing 330 and the second wing 360. The frame 302 can be further rotated so that the slots 332,334 are arranged to receive the spacer 320 such that a load applied to the spacer 320 is sufficiently distributed across the surface of the spacer 320 (i.e., the spacer 320 approximately conforms to a space between the contact surfaces of adjacent spinous processes 2,4 of the targeted motion segment).

Figure 3D:
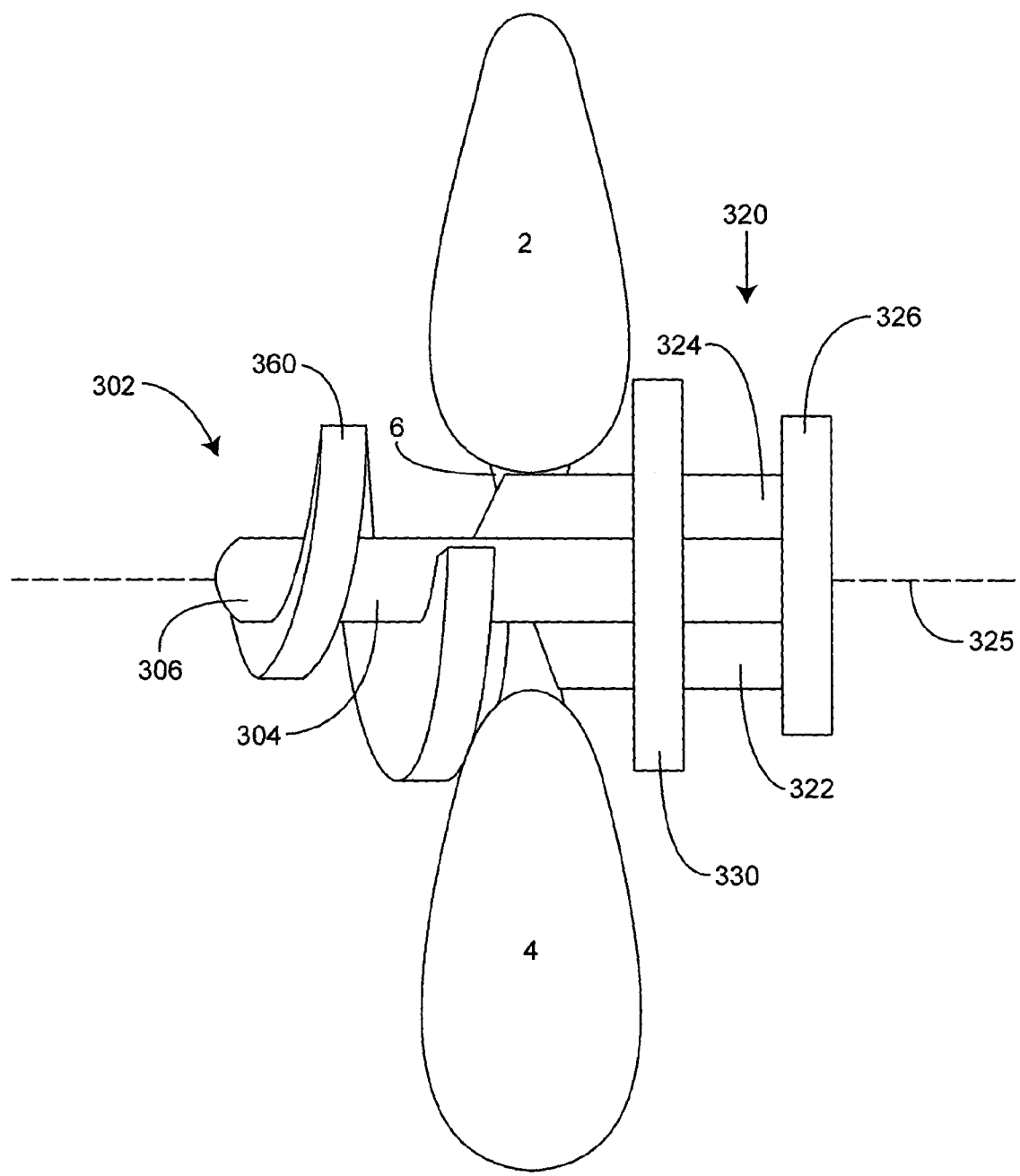
FIG. 3D partial cross-sectional posterior view of the frame of the implant of FIGS. 2A-2C wherein a spacer is partially arranged over a central body of the frame so that a portion of the spacer partially distracts the interspinous ligament.
Figure 3E:
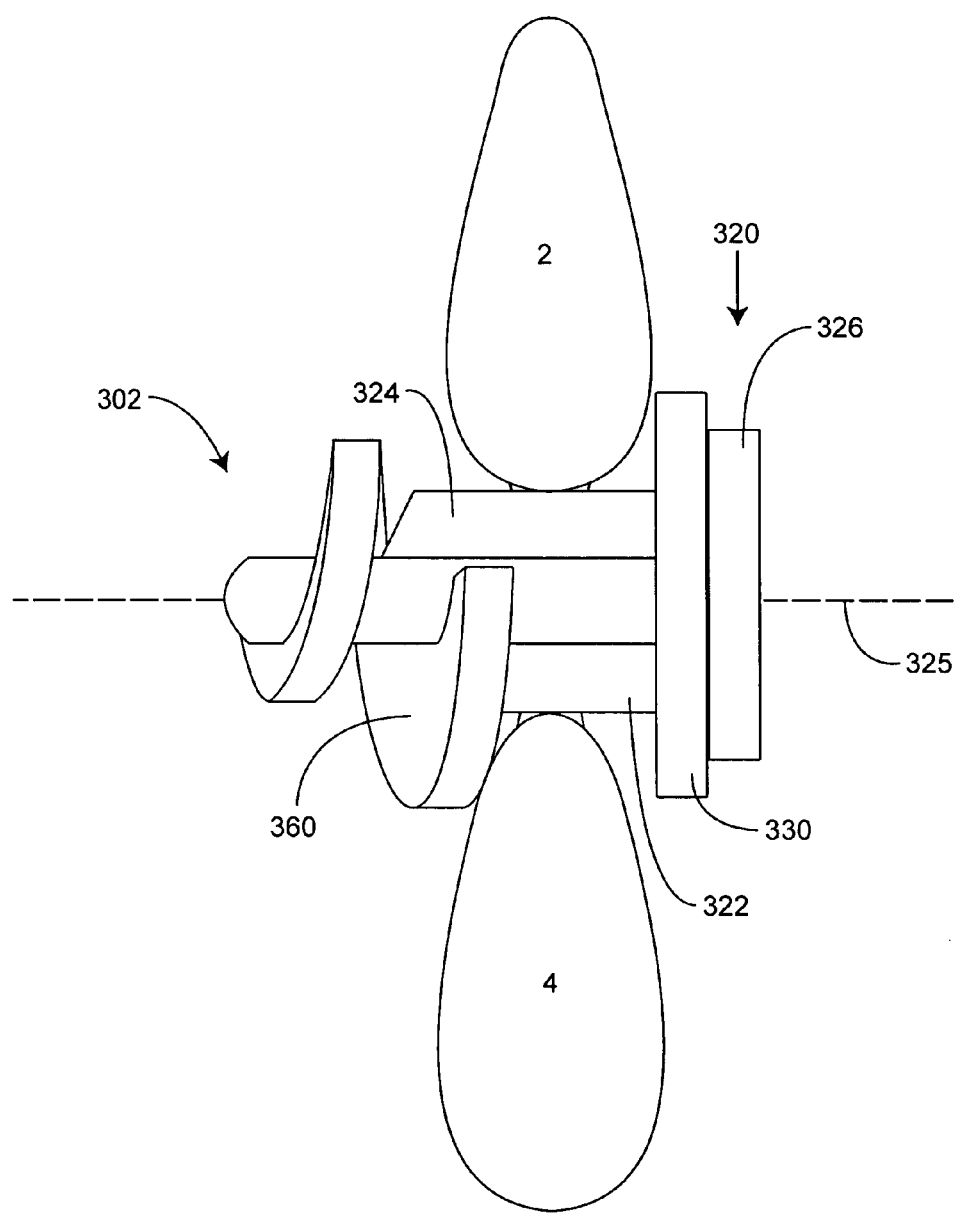
FIG. 3E partial cross-sectional posterior view of the frame of the implant of FIGS. 2A-2C wherein the spacer is seated over the central body of the frame so that a portion of the spacer partially distracts the interspinous ligament.

Referring to FIGS. 3D and 3E, once the frame 304 is arranged as desired, the top portion 322 and the bottom portion 324 can be positioned within the corresponding slots 332,334 and urged over the central body 304 so that the top portion 322 and bottom portion 324 further distract the interspinous ligament 6 and/or the adjacent spinous processes 2,4. The spacer 320 can be urged in the direction of insertion until the base 326 is seated against the first wing 330. In a preferred embodiment, the top portion 322 and the bottom portion 324 can be arranged so that the top portion 322 and bottom portion 324 are approximately in contact or near-contact with the second wing 360, so that the spacer 320 fully supports a load applied by the adjacent spinous processes 2,4, without slippage.

Figure 4A:
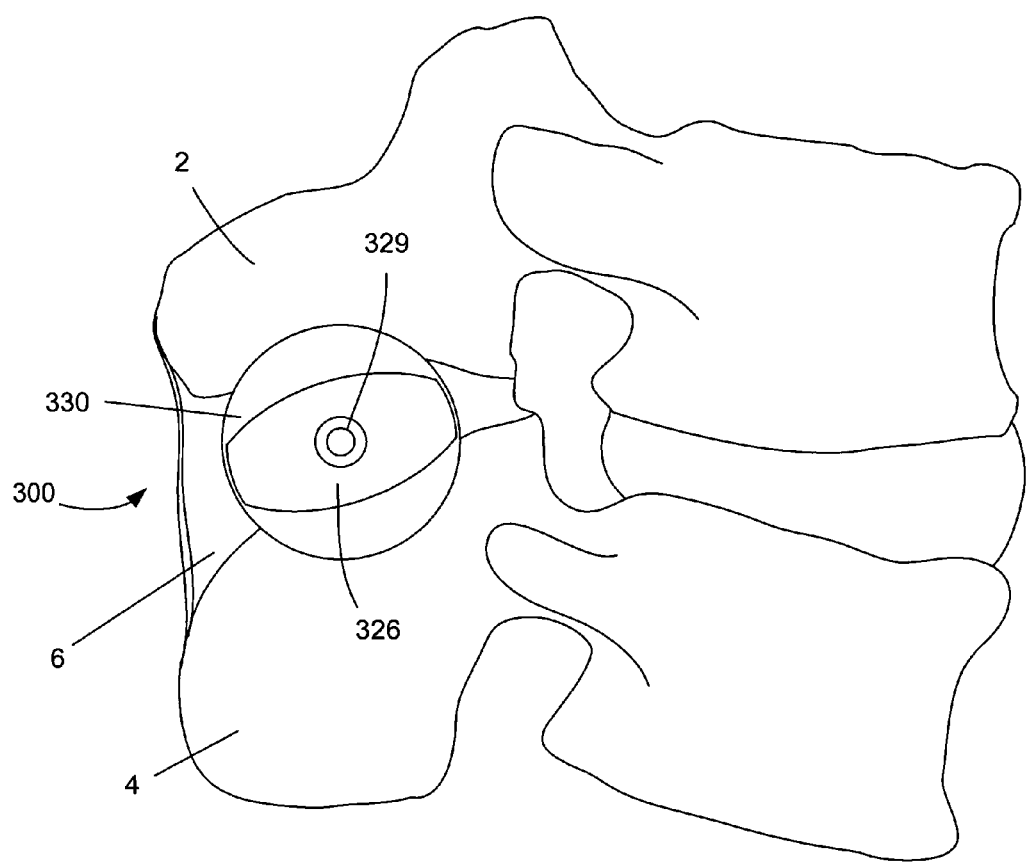
FIG. 4A is an end view of the implant of FIG. 3E positioned between adjacent spinous processes.

FIG. 4A is an end view of the implant 300 positioned between the adjacent spinous processes 2,4 of the targeted motion segment. As can be seen, the base 326 is arranged at a slight angle relative to the axis of the spine. As can be seen, the upper spinous process 2 includes a lower contact surface that arcs slightly downward, and the lower spinous process 4 includes an upper contact surface that also arcs slightly downward. Arranging the implant 300 as shown can increase the overall contact surface between the adjacent spinous processes 2,4 and the spacer 320 over, for example, inserting the implant 300 so that the base 326 is aligned perpendicular to the axis of the spine. Increasing overall contact surface can reduce the stress applied from the motion segment to the spacer 320, and from the spacer to the adjacent spinous processes 2,4.

As can further be seen, the base 326 can include a cavity 329 that in an embodiment is a bore having a diameter larger than a diameter of a corresponding cavity 309 of the first wing 330. Such a feature can be receive an insertion tool (not shown) for assisting in implantation, or such a feature can receive a fastener (not shown), such as a screw or bolt to secure the spacer 320 to the frame 302. A bore 329 having a larger diameter than the cavity 309 of the frame 302 can allow a head of the fastener to be received so that the head does not extend beyond a distal face of the base 326. In other embodiments, the base 326 can include one or more additional cavities for receiving lock pins, or other features of an insertion tool (not shown), for example as described in U.S. Pat. No. 6,712,819, entitled "Mating Insertion Instruments for Spinal Implants and Methods of Use," issued Mar. 30, 2004 to Zucherman, et al.

Figure 4B:
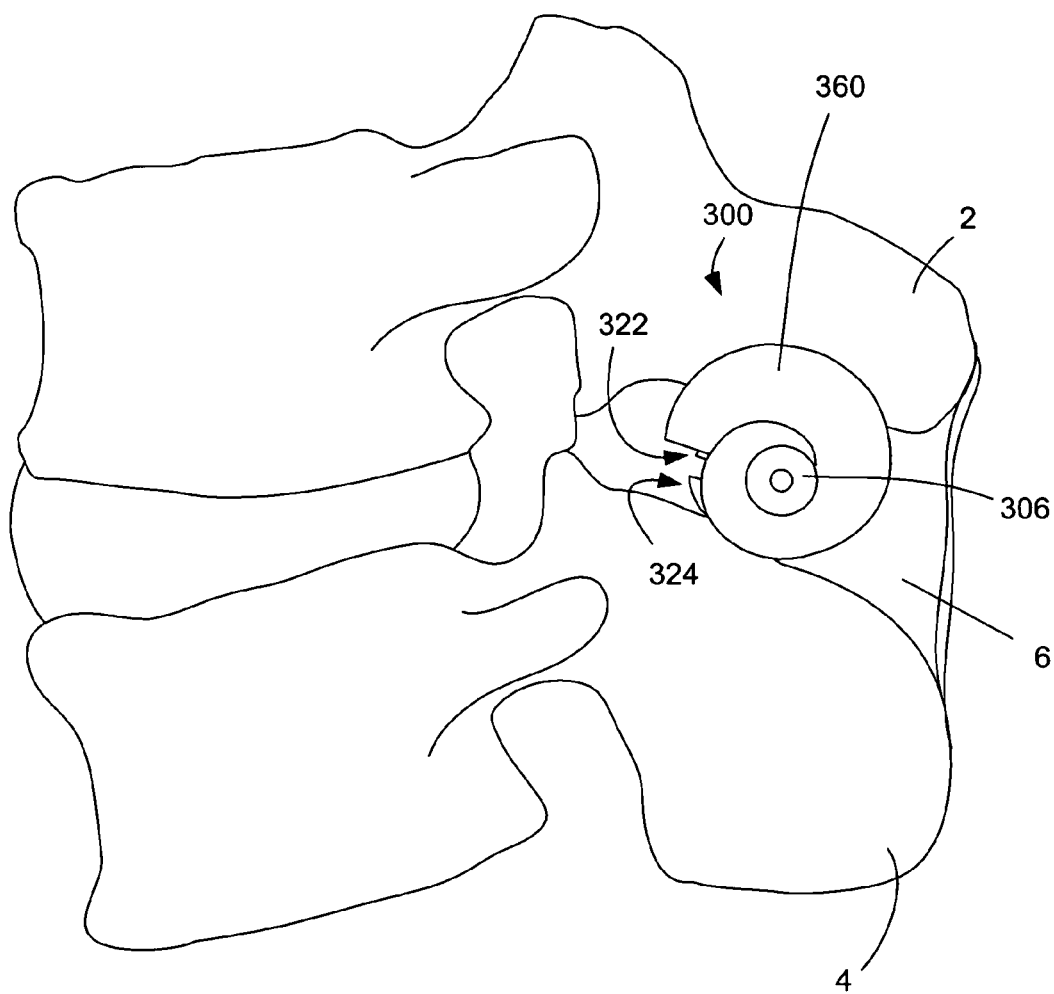
FIG. 4B is an front view of the implant of FIG. 3E positioned between adjacent spinous processes.

FIG. 4B is a front view of the implant 300 positioned between the adjacent spinous processes 2,4 of the targeted motion segment. As can be seen, the second wing 360 is helical in shape and can limit or block motion in a direction opposite insertion by contacting the upper spinous process 2. Further, a portion of the second wing 360 can contact the lower spinous process 4. Although the second wing 360 as shown includes a helical shape somewhat similar to that of a conch shell, in other embodiments the second wing 360 can have a shape that varies from the shape shown. For example, the distal end of the second wing 360 can overlap the proximal end of the second wing 360 more or less than as shown. Alternatively, the second wing 360 can be formed in two or more broken sections, rather than an unbroken spiral. Still further, the second wing 360 can include slots for receiving a proximal piece of the upper and lower portions 322,324 of the spacer 320. Myriad different variations of the shape shown in FIGS. 3A-4B will be readily apparent to one of skill in the art upon understanding the structure shown. Implants in accordance with the present invention are not intended to be limited to those described and shown herein, but rather apply to all such implants that utilize a wing having a major dimension larger than a major dimension of a space between spinous processes, wherein the wing can be appropriately positioned by rotating the implant while urging the implant in a direction of insertion.

Figure 5A:
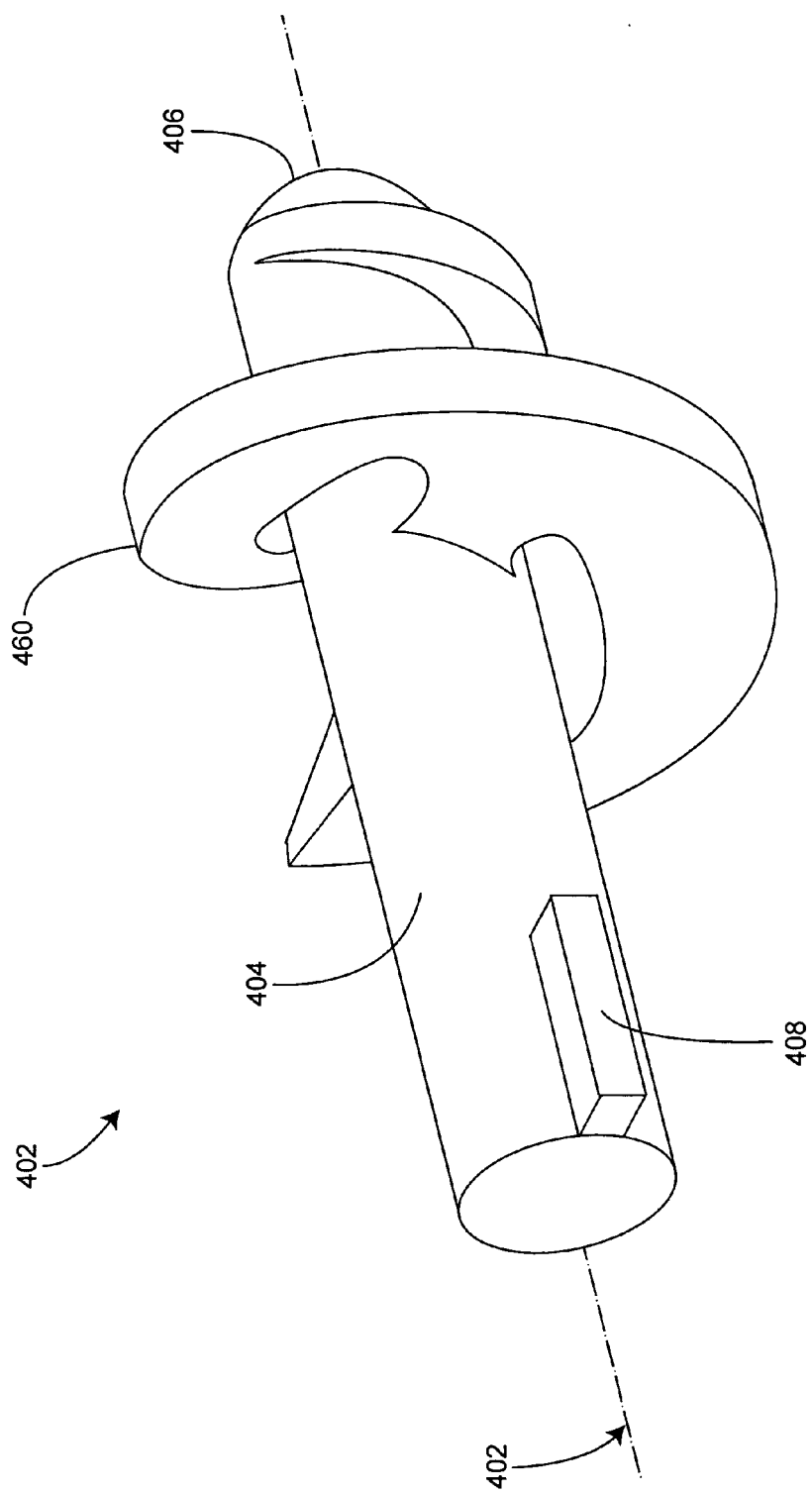
FIG. 5A is a perspective view of a frame from an alternative embodiment of an implant in accordance the present invention.
Figure 5B:
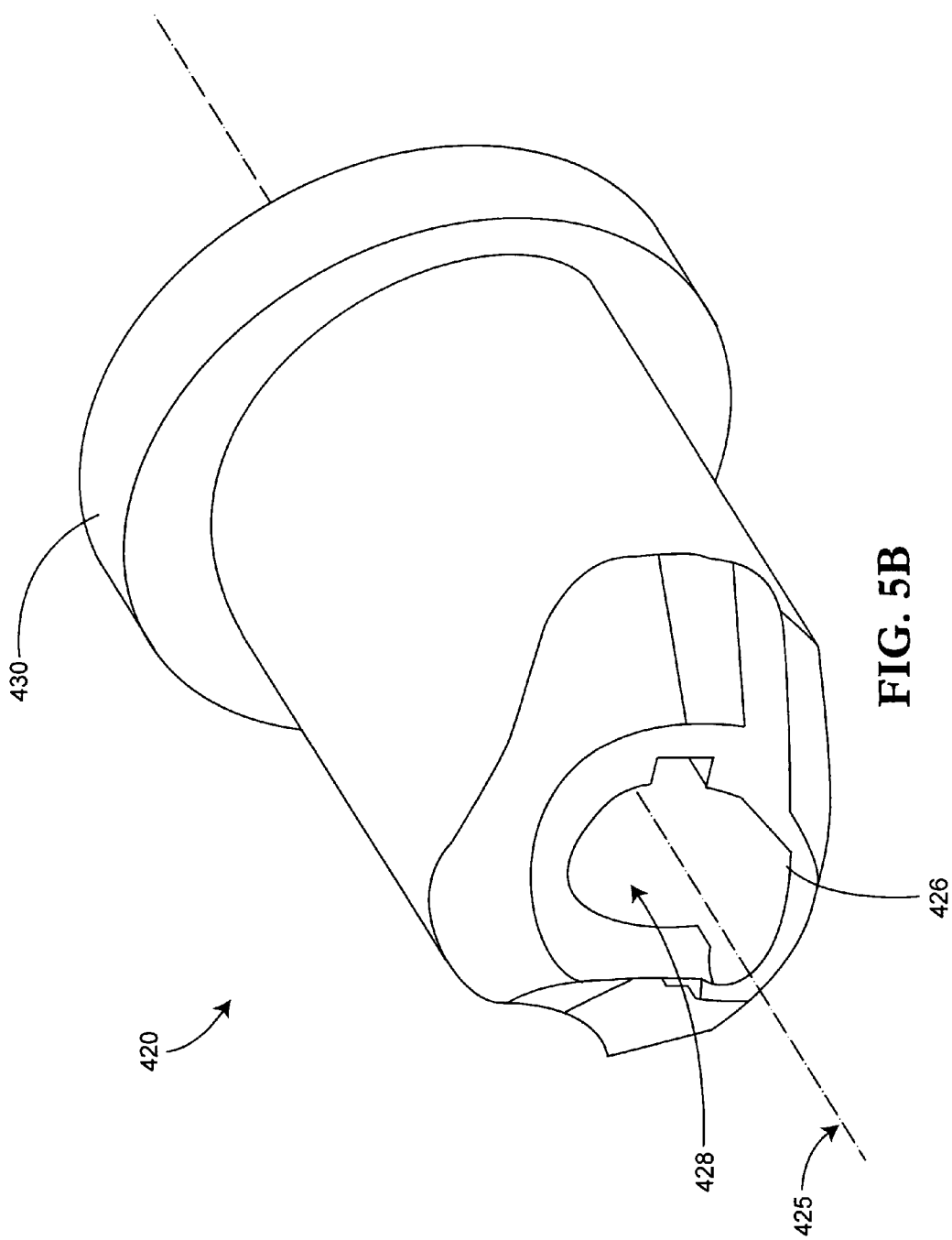
FIG. 5B is a perspective view of a spacer for use with the frame of FIG. 5A.
Figure 5C:
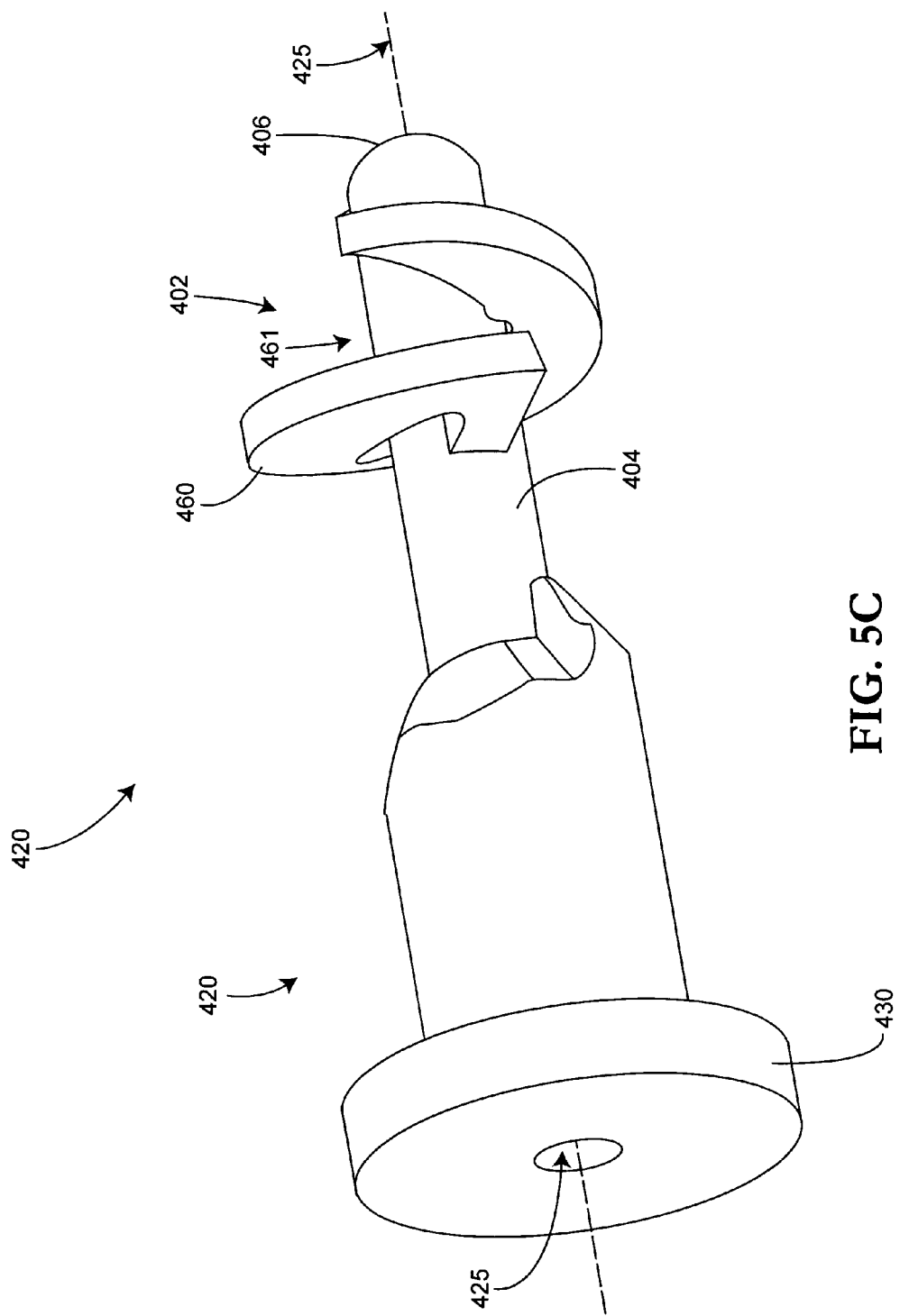
FIG. 5C is a perspective view of the spacer of FIG. 5B seated within the frame of FIG. 5A.

Referring now to FIGS. 5A through 5C, an alternative embodiment of an implant 400 in accordance with an embodiment of the present invention is shown. FIG. 5A is a perspective view of the frame 402 including a central body 404 having a distraction guide 406 at a proximal end, and an alignment protrusion 408 at a distal end. As can be seen, the second wing 460 is similar to the second wing 460 described above. The alignment protrusion 408 extends from the central body 404 to align a spacer 420 as the spacer 420 is arranged over the central body 404, and to prevent the spacer 420 from subsequently rotating relative to the frame 402 once implanted. Thus, the alignment protrusion 408 corresponds to a notch 427 within the spacer 420 within which the central body 404 is partially disposed.

FIG. 5B is a perspective view of the spacer 420. The spacer 420 includes a bore 428 disposed at least partially through the spacer 420, and including a notch 427 along the length of the bore 428 to receive the alignment protrusion 408 of the frame 402. The proximal end of the spacer 420 can be tapered to form a distraction guide 426 to distract the interspinous ligament 6 and/or the adjacent spinous processes 2,4 of the motion segment. Similarly to the rotatable spacer 220 of FIG.

1B, and the implant 300 of FIGS. 2A-2C, the implant 400 can be further rotated or adjusted to distribute a load once the spacer 420 is positioned over the frame 404 and between the spinous processes 2,4.

As above, the spacer 420 can have a cross-section perpendicular to the longitudinal axis 425 that is teardrop-shaped, similar to a cross-section of the spacer 120,320 of FIGS. 1A and 2A. In this way, the shape of the spacer 420 can roughly conform to a wedge-shaped space, or a portion of the space, between adjacent spinous processes 2,4 within which the implant 400 is to be positioned. The same shape or variations of this shape can be used to accommodate different motion segments and/or different patients, as described above. In other embodiments the spacer 420 can have alternative shapes such as circular, elliptical, wedge, oval, ovoid, football, and rectangular with rounded corners, and other shapes. The shape of the spacer 420 can be selected for a particular patient so that the physician can position the implant 400 as close as possible to the anterior portion of the surface of the spinous process 2,4. The shape selected for the spacer 420 can affect the contact surface area of the implant 400 and the spinous processes 2,4 that are to be subject to distraction. Increasing the contact surface area between the implant 400 and the spinous processes 2,4 can distribute a load force between the spinous frame and the implant 400.

The spacer 420 of FIG. 5B extends from a first wing 430 integrally formed or connected with the spacer 420. As can be seen, a proximal end of the spacer 420 varies in length, extending farther near the bottom section of the spacer 420 to correspond roughly with the helical shape of the second wing 460, thereby avoiding contacting the second wing 460 which in the embodiment shown in FIG. 5A spirals to a termination point at the upper surface of the central body 404. As above, once the frame 404 is arranged as desired, the spacer 420 can be positioned over the central body 404 and urged over the central body 404 so that the spacer 420 further distracts the interspinous ligament and/or the adjacent spinous processes. The spacer 320 can be urged in the direction of insertion until the central body 404 is seated within the bore 428. In a preferred embodiment, the shape of the proximal end of the spacer 420 is shaped such that when seated, the proximal end is approximately in contact or near-contact with the second wing 460, so that the spacer 420 fully supports a load applied by the adjacent spinous processes, without slippage.

The first wing 430 can have a depth along the longitudinal axis 425 as desired, and a width such that the first wing 430 can contact one or both of the adjacent spinous processes 2,4, thereby limiting or blocking moving of the implant 400 in the direction of insertion along the longitudinal axis 425. As shown, the first wing 430 has a rounded shape, having substantially the same minor and major dimension. Unlike the embodiment of the implant 300 of FIGS. 2A-2C, the first wing 430 need not rotate to properly arrange the second wing 460, therefore the first wing 430 need not have a round shape, where it is desired that the second wing 460 have some other shape. For example, the first wing 430 can include a shape similar to that shown in FIG. 1B. The first wing 430 can include a cavity 429 for receiving one or both of an insertion tool (not shown). Further, the central body 404 can optionally include a cavity 409 so that, for example, the frame 402, the spacer 420, and the first wing 430 can be fixedly attached once the spacer 420 is seated.

Figure 6:
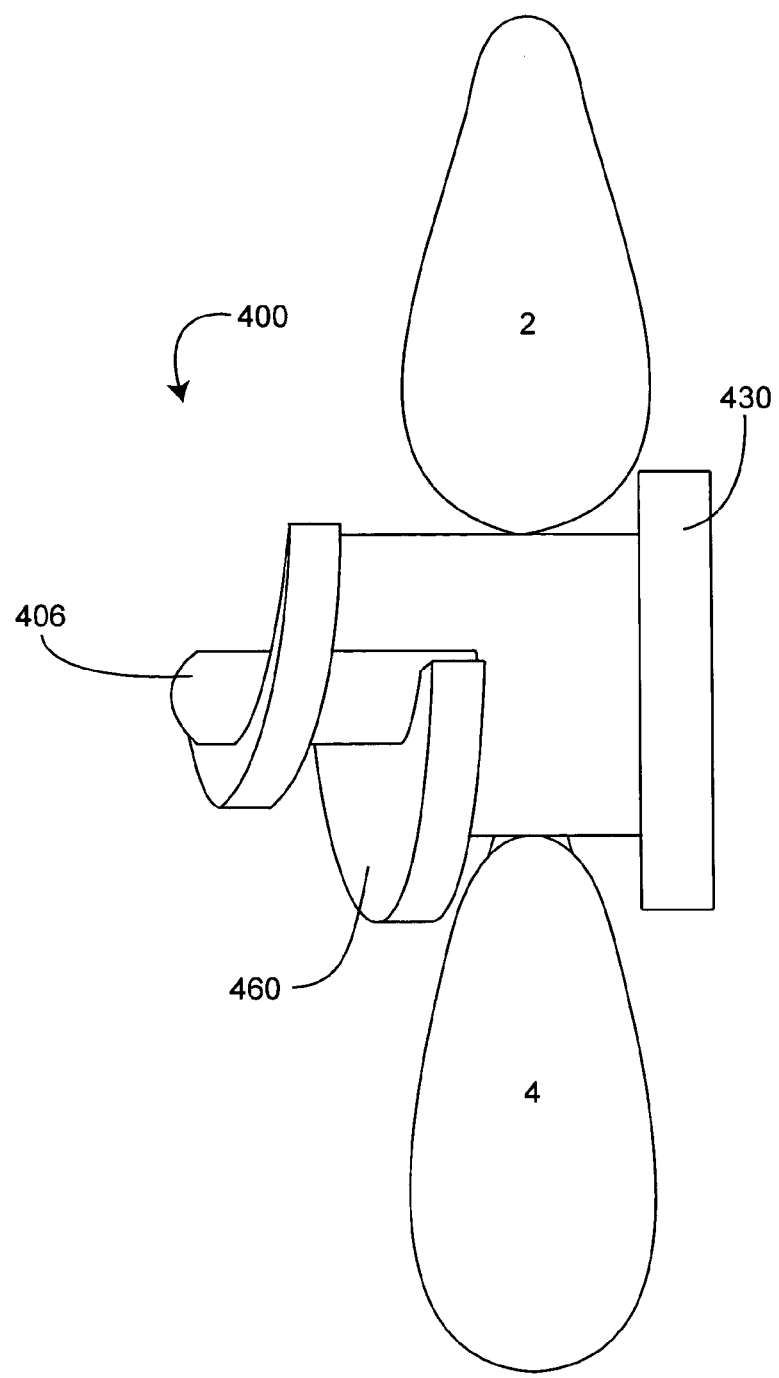
FIG. 6 is a side view of the implant of FIGS. 5A-5C positioned between adjacent spinous processes.

FIG. 5C is a perspective view of the implant 400 wherein the spacer 420 is positioned to be seated on the frame 402 and arranged over the central body 404. The first wing 430 and the second wing 460 have major dimensions approximately along the axis of the spine that are larger than the major dimension of the spacer 420, thereby blocking or limiting movement of the implant 400 along the longitudinal axis 425. FIG. 6 is a posterior view of an implant 400 as described in FIGS. 5A-5C disposed between the adjacent spinous processes.

In some embodiments of systems including implants 300, 400 similar to those shown in FIGS. 2A-5C, multiple different spacers 320,420 can be selectively associated with a single frame 302,402 so that a physician can choose an appropriately sized and shaped spacer 320,420 to accommodate a patient's anatomy. In embodiments including a central body 304 extending from a first wing 330, the distance between the outer peripheries of the two slots 332,334 can correspond to a maximum spacer size (e.g., 14 mm). In embodiments including a central body 404 having an alignment protrusion 408, a series of spacer 420 can have varying dimensions and/or shapes, and can have similarly sized cavities 428 to receive the central body 404. As can be readily understood from this description, a system in accordance with embodiments of the present invention can include a frame 302,402 and a plurality of spacers 320,420 having varying sizes and/or shapes.

Figure 7A:
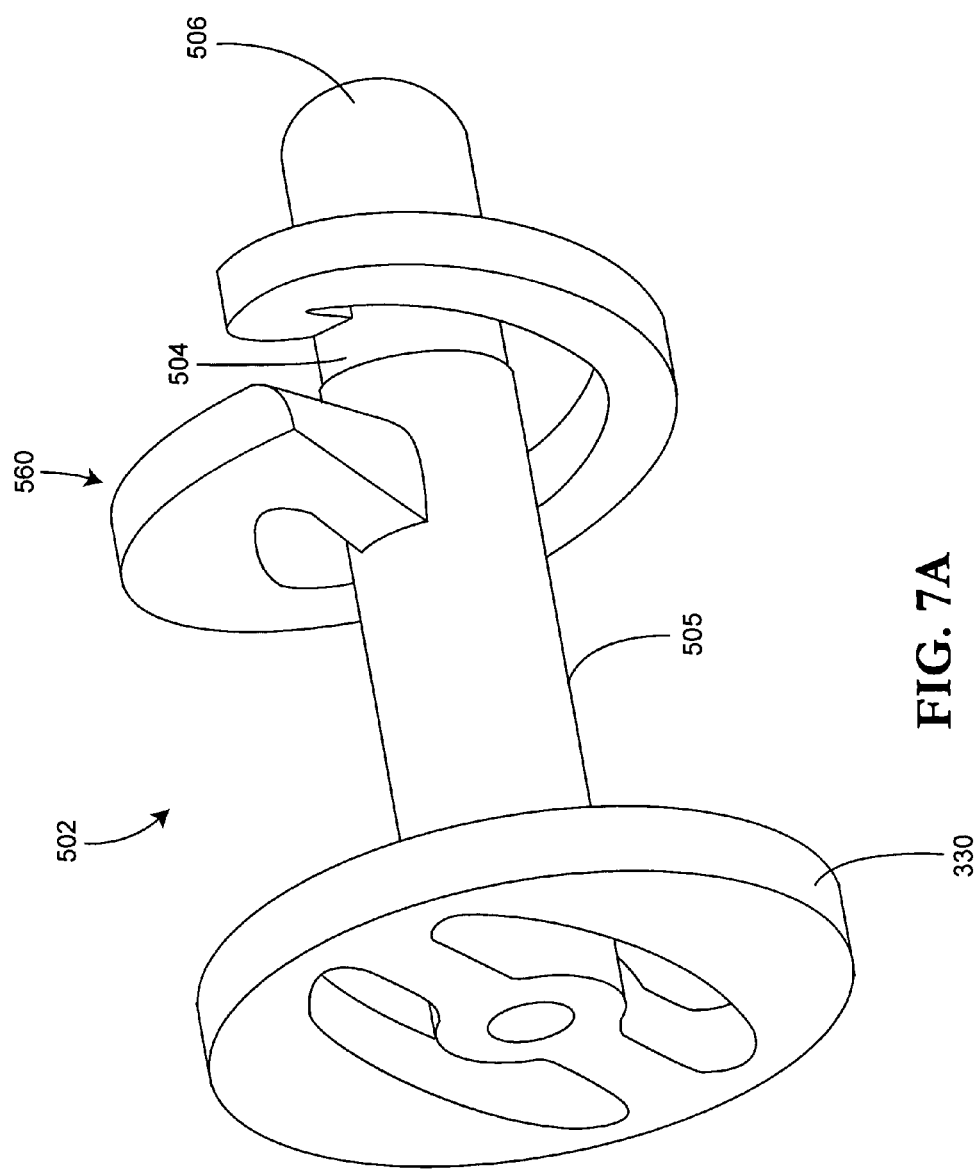
FIG. 7A is a perspective view of a frame from a still further embodiment of an implant in accordance with the present invention.
Figure 7B:
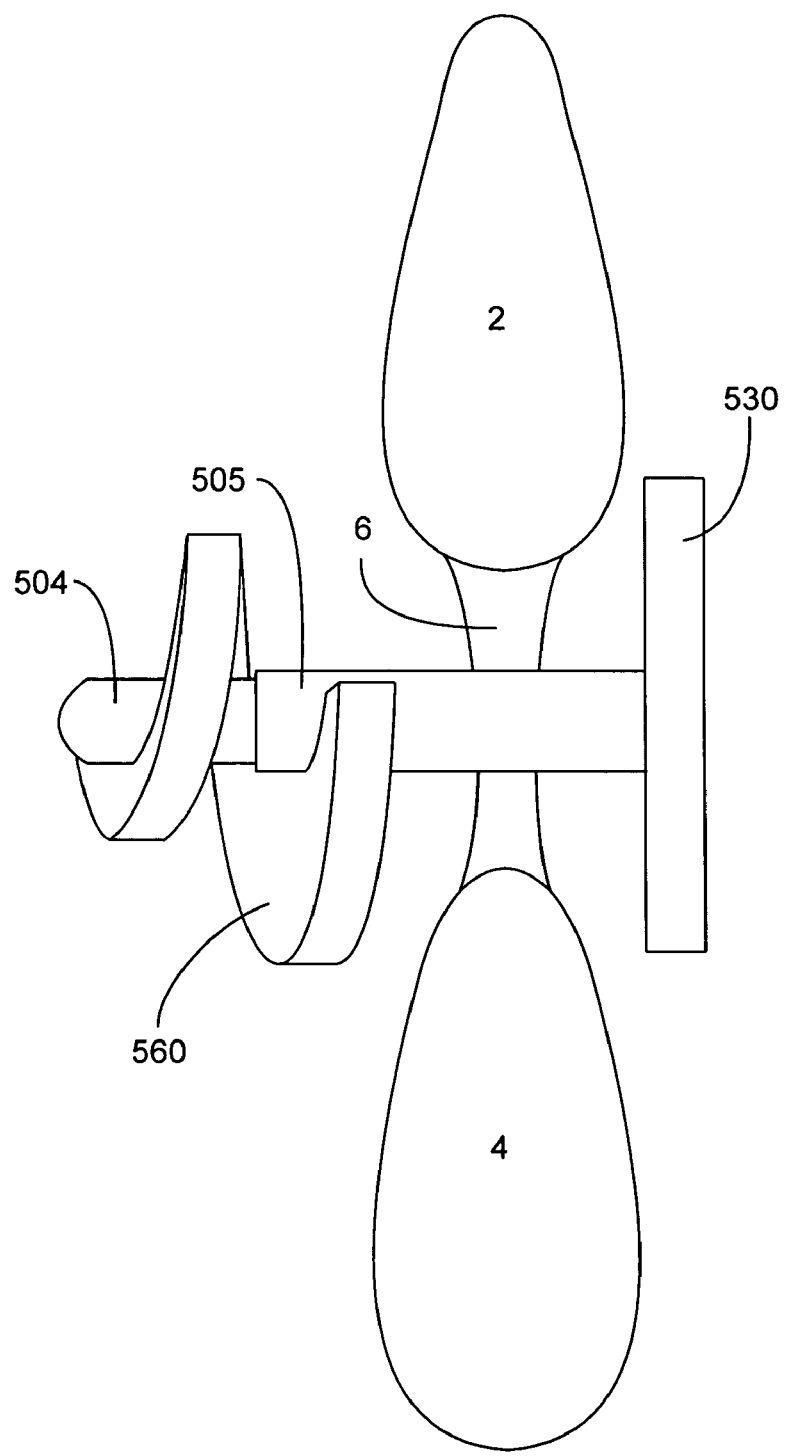
FIG. 7B is a side view of the frame of FIG. 7A positioned between adjacent spinous processes.
Figure 7C:
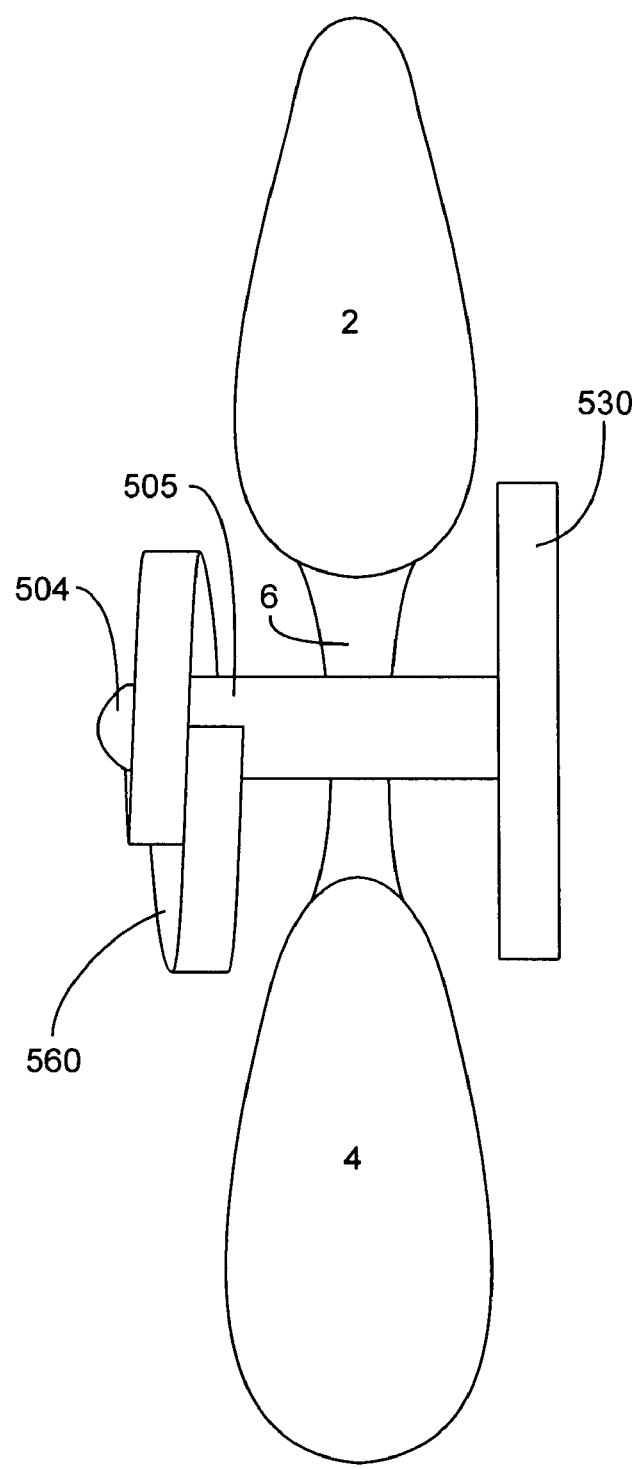
FIG. 7C is a side view of the frame of FIG. 7A positioned between adjacent spinous processes and retracted to collapse the second wing.

As mentioned above, implants, and systems and methods for positioning such implants between spinous processes in accordance with the present invention are not meant to be limited to embodiments as described above and otherwise herein, but rather are meant to include all such implants that utilize a wing having a major dimension larger than a major dimension of a space between spinous processes, wherein the wing can be appropriately positioned by rotating the implant while urging the implant in a direction of insertion. Myriad different variations may be readily apparent to one of ordinary skill in the art. For example, as shown in FIGS. 7A through 7C, in still another embodiment of an implant 500 in accordance with the present invention, the frame 502 can include an inner central body 504 disposed within an outer central body 505, with a proximal portion of a second wing 560 being connected with, or extending from the inner central body 504, and the distal portion of the second wing 560 being connected with, or extending from the outer central body 505. Once the frame 502 is arranged as desired, such that the interspinous ligament is disposed between a first wing 330 and the second wing 560, the inner central body 504 can be shifted to a position more fully received in the outer central body 505 so that the second wing 560 collapses, reducing the space occupied by the second wing 560.

In such embodiments as shown in FIGS. 7A through 7C, the second wing 560 can be made from a more ductile material so that the second wing 560 can be readily collapsed. Alternatively, the second wing 560 can be made from a shape memory material, for example such as Nitinol, so that once the frame is positioned the second wing 560 collapses, urging the inner central body 504 to shift within the outer central body 505. Additionally the second wing 560 can be made in two parts, one part fastened to the inner central body 504, and one part fastened to the outer central body 505. When the inner central body 504 is more fully received into the outer central body 505, the portion of the second wing 560 secure to the inner central body 504 becomes nested in the portion of the second wing 560 connected to the outer central body 505.

Figure 8:
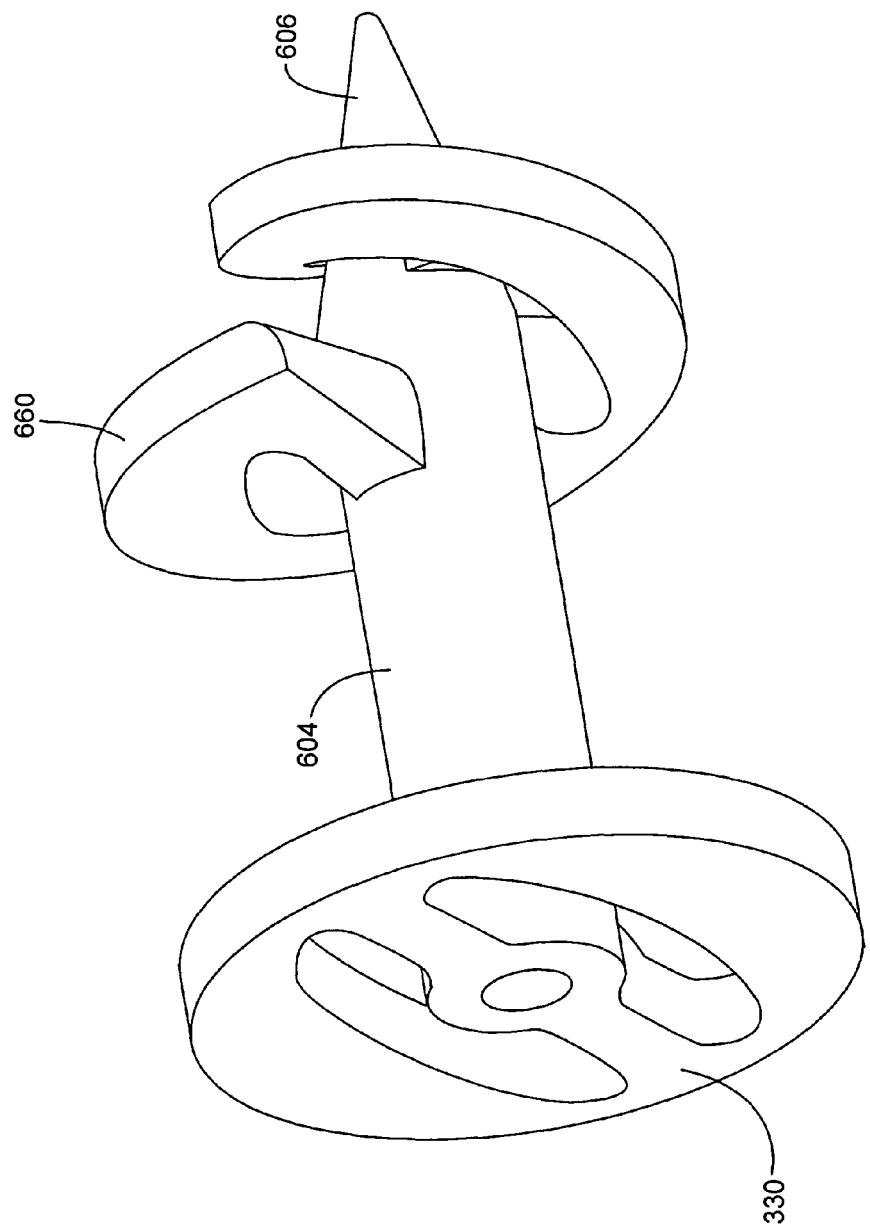
FIG. 8 is a perspective view of a frame from a still further embodiment of an implant in accordance with the present invention.

As shown in FIG. 8, in a still further embodiment an implant 600 in accordance with the present invention can include a distraction guide 606 that tapers more gradually, so that the adjacent spinous processes and/or related tissues are distracted as the lead-in screw 660 is rotated and urged toward a direction of insertion, as described above.

In still further embodiments, the spacer need not be fixed, but rather can be rotatably disposed over the central body. For example, the spacer can include an alignment notch, as described above with reference to FIG. 1B, so that when the central body is rotated, thereby threading the adjacent spinous processes and related structures within the groove of the thread-shaped wing and positioning the thread-shaped wing on an opposite side of the adjacent spinous processes, the spacer can be held in a fixed positioned. By fixing the spacer is position, the spacer can be arranged as desired between the adjacent spinous processes. Once the implant is positioned between adjacent spinous processes, the rotatable spacer can be released to conform within the space between spinous processes. These and other variations are within the scope of the invention as contemplated.

Materials for Use in Implants of the Present Invention

In some embodiments, the implant, and components of the implant (i.e., the spacer, the frame) can be fabricated from medical grade metals such as titanium, stainless steel, cobalt chrome, and alloys thereof, or other suitable implant material having similar high strength and biocompatible properties. Additionally, the implant can be at least partially fabricated from a shape memory metal, for example Nitinol, which is a combination of titanium and nickel. Such materials are typically radiopaque, and appear during x-ray imaging, and other types of imaging. Implants in accordance with the present invention, and/or portions thereof can also be fabricated from somewhat flexible and/or deflectable material. In these embodiments, the implant and/or portions thereof can be fabricated in whole or in part from medical grade biocompatible polymers, copolymers, blends, and composites of polymers. A copolymer is a polymer derived from more than one species of monomer. A polymer composite is a heterogeneous combination of two or more materials, wherein the constituents are not miscible, and therefore exhibit an interface between one another. A polymer blend is a macroscopically homogeneous mixture of two or more different species of polymer. Many polymers, copolymers, blends, and composites of polymers are radiolucent and do not appear during x-ray or other types of imaging. Implants comprising such materials can provide a physician with a less obstructed view of the spine under imaging, than with an implant comprising radiopaque materials entirely. However, the implant need not comprise any radiolucent materials.

One group of biocompatible polymers is the polyaryletherketone group which has several members including polyetheretherketone (PEEK), and polyetherketoneketone (PEKK). PEEK is proven as a durable material for implants, and meets the criterion of biocompatibility. Medical grade PEEK is available from Victrex Corporation of Lancashire, Great Britain under the product name PEEK-OPTIMA. Medical grade PEKK is available from Oxford Performance Materials under the name OXPEKK, and also from CoorsTek under the name BioPEKK. These medical grade materials are also available as reinforced polymer resins, such reinforced resins displaying even greater material strength. In an embodiment, the implant can be fabricated from PEEK 450G, which is an unfilled PEEK approved for medical implantation available from Victrex. Other sources of this material include Gharda located in Panoli, India. PEEK 450G has the following approximate

| Property | Value |
|---|---|
| Density | 1.3 g/cc |
| Rockwell M | 99 |
| Rockwell R | 126 |
| Tensile Strength | 97 MPa |
| Modulus of Elasticity | 3.5 GPa |
| Flexural Modulus | 4.1 GPa |

PEEK 450G has appropriate physical and mechanical properties and is suitable for carrying and spreading a physical load between the adjacent spinous processes. The implant and/or portions thereof can be formed by extrusion, injection, compression molding and/or machining techniques.

It should be noted that the material selected can also be filled. Fillers can be added to a polymer, copolymer, polymer blend, or polymer composite to reinforce a polymeric material. Fillers are added to modify properties such as mechanical, optical, and thermal properties. For example, carbon fibers can be added to reinforce polymers mechanically to enhance strength for certain uses, such as for load bearing devices. In some embodiments, other grades of PEEK are available and contemplated for use in implants in accordance with the present invention, such as 30% glass-filled or 30% carbon-filled grades, provided such materials are cleared for use in implantable devices by the FDA, or other regulatory body. Glass-filled PEEK reduces the expansion rate and increases the flexural modulus of PEEK relative to unfilled PEEK. The resulting product is known to be ideal for improved strength, stiffness, or stability. Carbon-filled PEEK is known to have enhanced compressive strength and stiffness, and a lower expansion rate relative to unfilled PEEK. Carbon-filled PEEK also offers wear resistance and load carrying capability.

As will be appreciated, other suitable similarly biocompatible thermoplastic or thermoplastic polycondensate materials that resist fatigue, have good memory, are flexible, and/or deflectable, have very low moisture absorption, and good wear and/or abrasion resistance, can be used without departing from the scope of the invention. As mentioned, the implant can be comprised of polyetherketoneketone (PEKK). Other material that can be used include polyetherketone (PEK), polyetherketoneetherketoneketone (PEKEKK), polyetheretherketoneketone (PEEKK), and generally a polyaryletheretherketone. Further, other polyketones can be used as well as other thermoplastics. Reference to appropriate polymers that can be used in the implant can be made to the following documents, all of which are incorporated herein by reference. These documents include: PCT Publication WO 02/02158 A1, dated Jan. 10, 2002, entitled "Bio-Compatible Polymeric Materials;" PCT Publication WO 02/00275 A1, dated Jan. 3, 2002, entitled "Bio-Compatible Polymeric Materials;" and, PCT Publication WO 02/00270 A1, dated Jan. 3, 2002, entitled "Bio-Compatible Polymeric Materials." Other materials such as Bionate®, polycarbonate urethane, available from the Polymer Technology Group, Berkeley, Calif., may also be appropriate because of the good oxidative stability, biocompatibility, mechanical strength and abrasion resistance. Other thermoplastic materials and other high molecular weight polymers can be used.

Methods for Implanting Interspinous Implants

Figure 9:
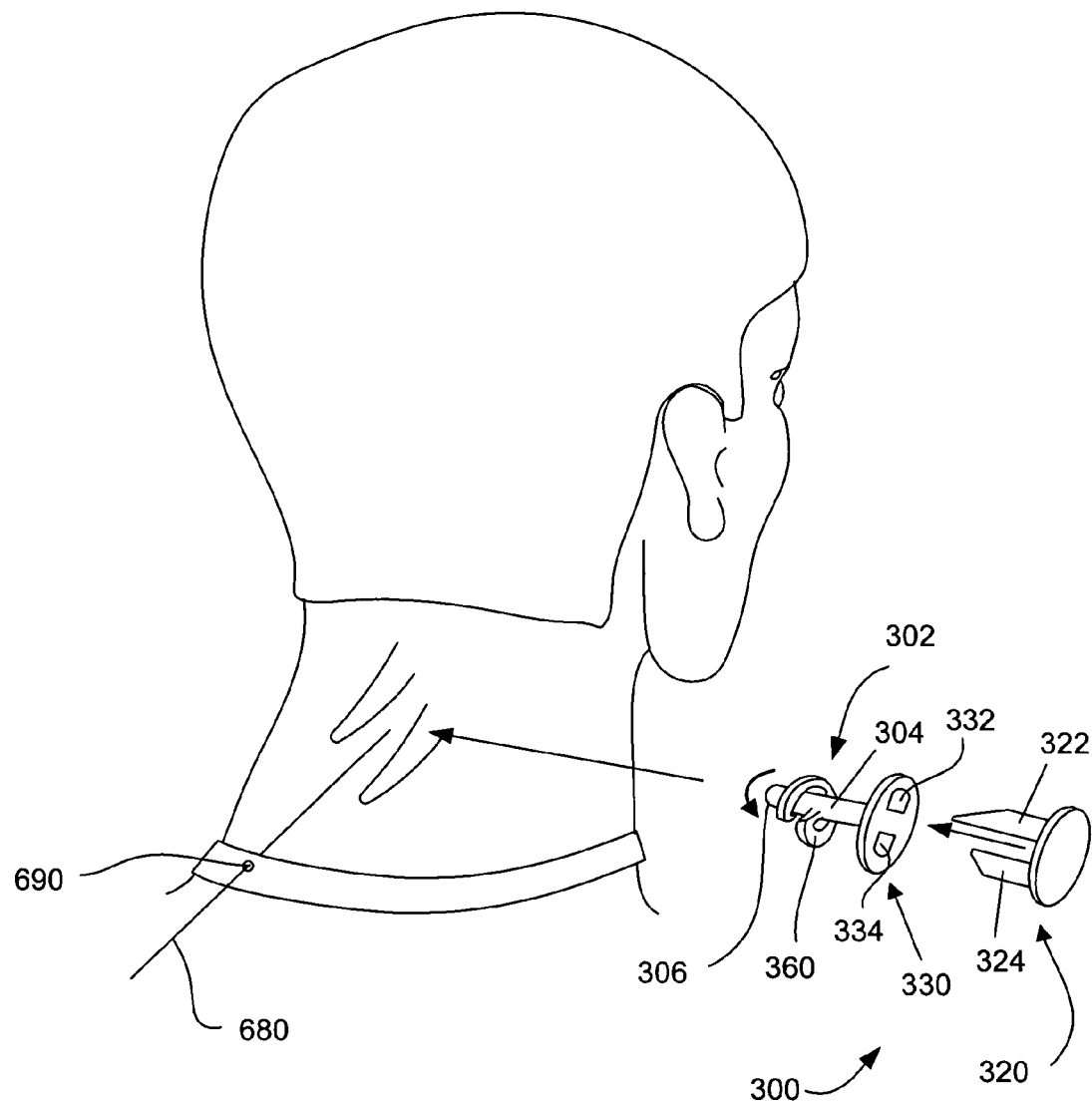
FIG. 9 illustrates an embodiment of a method for implanting an interspinous implant between adjacent spinous processes of the cervical region in accordance with the present invention.

A minimally invasive surgical method for implanting an implant 300 in the cervical spine is disclosed and taught herein. In this method, as shown in FIG. 9, preferably a guide wire 680 is inserted through a placement network 690 into the neck of the implant recipient. The guide wire 680 is used to locate where the implant 300 is to be placed relative to the cervical spine, including the spinous processes. Once the guide wire 680 is positioned with the aid of imaging techniques, an incision is made on the side of the neck so that an implant 300 in accordance with an embodiment of the present invention, can be positioned in the neck thorough an incision and along a line that is about perpendicular to the guide wire 680 and directed at the end of the guide wire 680. A frame 302 of the implant 300 is inserted into the neck of the patient. The frame 302 includes a distraction guide 306 extending from the proximal end of a central body 304 and a first wing 330 extending from the distal end of the central body 304. The frame 302 further includes a helical-shaped second wing 360 extending distally from the distraction guide 306 some distance along the central body 304. Preferably during insertion, the distraction guide 306 pierces or separates the tissue without severing the tissue. The frame 302 can be arranged so that the second wing 360 extending from the central body 304 is in contact or near contact with the interspinous ligament. The frame 302 is then rotated in a direction so that the spiraling extension of the second wing 360 "grows" and the frame 302 is urged forward such that the adjacent spinous processes fit within a groove between spiraled surfaces of the second wing 360. The frame 302 is continuously rotated until the second wing 360 has passed the adjacent spinous processes 2,4.

The frame 302 can be further rotated until slots 332,334 of the first wing 330 are arranged as desired between the adjacent spinous processes 2,4 of the targeted motion segment. Once the frame 302 is satisfactorily positioned, a spacer 320 can be mated with the frame 302 so that an upper portion 322 and a lower portion 324 of the spacer 320 is received through the respective slot 332,334 of the first wing 330 (or simply received over the central body 304 for example where the first wing 330 extends from the spacer 320 rather than extending form the central body 304). The spacer 320 can be inserted along a line that is generally colinear with the line over which the frame 302 is inserted. The anatomy of the neck is such that it is most convenient and minimally invasive to enter the neck from the side with respect to the frame 302 and the spacer 320.

Figure 10:
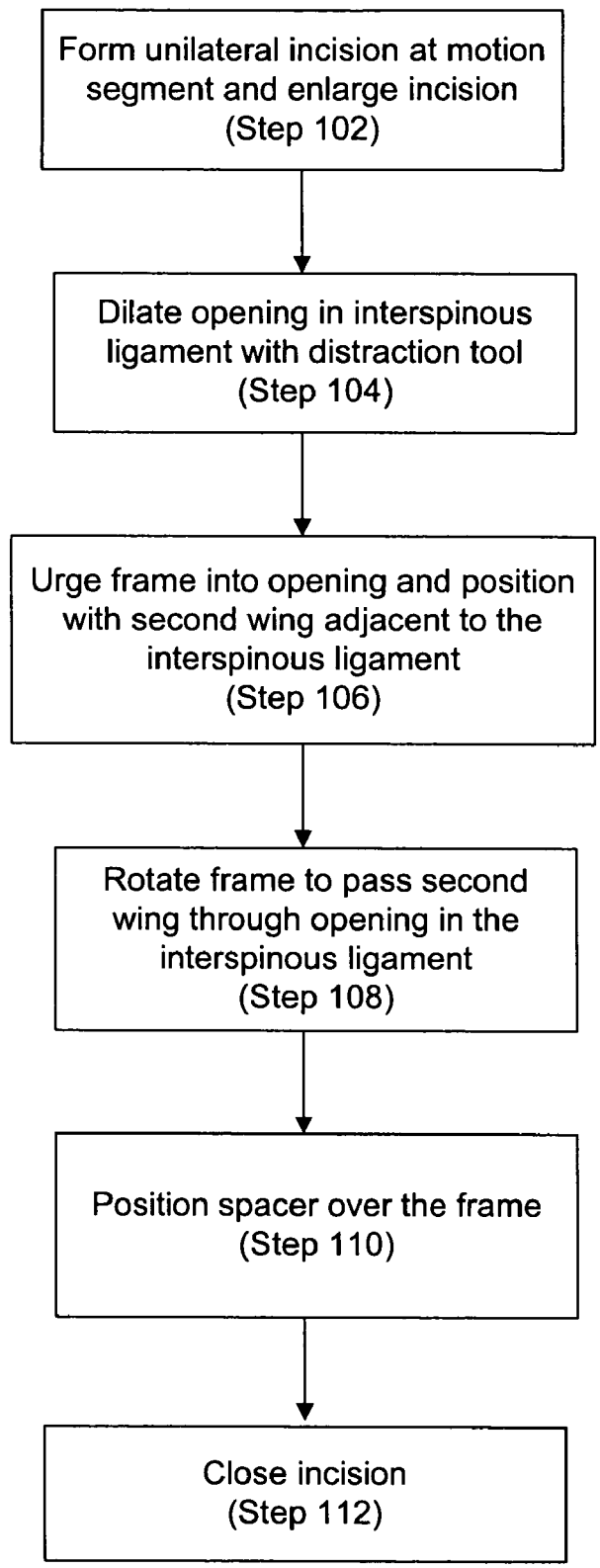
FIG. 10 is a flowchart of a method for implanting an interspinous implant between adjacent spinous processes of the lumbar region in accordance with the present invention.

Further, a minimally invasive surgical method for implanting an implant 300 in the lumbar spine is disclosed and taught herein. In this method, as shown in the flowchart of FIG. 10, preferably a unilateral incision can be made using a posterior-anterior approach. The unilateral incision can be made, for example, at a location some distance to the right of an axis along the spinous process 2,4 (Step 102). The incision can be enlarged, and a distraction tool can be positioned within the incision so that the proximal end of the distraction tool can access an exposed side of the interspinous ligament 6. The distraction tool can be urged through the interspinous ligament 6 and distracted, thereby distracting the interspinous ligament 6 so as to receive the implant 300 (Step 104). Once the interspinous ligament 6 is sufficiently distracted, the distraction tool can be disengaged and removed from the incision.

Once the distraction tool has been removed from the incision, the frame 302 can be positioned at the dilated opening, and the distraction guide 306 of the frame 302 can be urged through the dilated opening (Step 106). As above, the frame 302 can be arranged so that the second wing 360 extending from the central body 304 is in near contact with the interspinous ligament 6. The frame 302 is then rotated in direction so that the spiraling extension of the second wing 360 "grows", and the frame 302 urged forward such that the adjacent spinous processes 2,4 fit within a groove between surface of the second wing 360 (Step 108). The frame 302 is continuously rotated until the second wing 360 has passed the adjacent spinous processes 2,4.

The frame 300 can be further rotated until the slots 332,334 are arranged as desired between the adjacent spinous processes of the targeted motion segment. The frame 302 is free to rotate so that the load can be distributed more evenly over the surface of the spinous processes. Once the frame 302 is satisfactorily positioned, a spacer 320 can be inserted with slots 322,324 of a first wing 330 extending from the distal end of the central body 304 (or simply received over the central body for example where the first wing extends from the spacer). The spacer 320 can be inserted along a line that is generally colinear with the line over which the frame 302 is inserted (Step 110). The remaining tools can be removed from the incision, and the incision can be closed. Preferably during insertion, the distraction end pierces or separates the tissue without severing the tissue (Step 112).

The foregoing description of the present invention have been presented for purposes of illustration and description. It is not intended to be exhaustive or to limit the invention to the precise forms disclosed. Many modifications and variations will be apparent to practitioners skilled in this art. The embodiments were chosen and described in order to best explain the principles of the invention and its practical application, thereby enabling others skilled in the art to understand the invention for various embodiments and with various modifications as are suited to the particular use contemplated. It is intended that the scope of the invention be defined by the following claims and their equivalents.

What is claimed:

1. An interspinous implant adapted to be inserted between spinous processes, the implant comprising:
    a frame including:
        a central body having a first end and a second end;
        a first wing extending from the second end; the first wing including a first slot and a second slot;
        a second wing extending from the first end; wherein the second wing is approximately thread-shaped;
    a spacer adapted to be associated with the frame such that the spacer is received over at least a portion of the central body; the spacer includes a first portion adapted to be received over the central body through the first slot and a second portion adapted to be received over the central body through the second slot.

2. The implant of claim 1 wherein the second wing has successive turns that are longitudinally spaced from each other so as to define a groove that curves around the longitudinal axis.

3. The implant of claim 1 wherein the second wing is helical.

4. The implant of claim 3 wherein the second wing extends a substantially constant distance from the longitudinal axis.

5. The implant of claim 1 wherein the spacer longitudinally spans substantially all of the distance between the first and second wings.

6. The implant of claim 1 wherein the second wing is movable between an expanded configuration and a collapsed configuration.

7. The implant of claim 1:
    wherein the central body has a longitudinal axis extending between the first end and the second end;
    wherein the first wing is larger in a dimension perpendicular to the longitudinal axis than the spacer;
    wherein the first end comprises a tapered distraction guide that narrowingly tapers away from the second end.

8. The implant of claim 1 wherein the spacer is sized and configured to span a majority of a length of the central body between the first wing and the second wing.

9. The implant of claim 1 wherein the spacer includes a longitudinal cavity.

10. The implant of claim 1 wherein the implant comprises Nitinol and a biocompatible polymer.

11. The implant of claim 10 wherein the biocompatible polymer is PEEK.

* * * * *